(12) United States Patent
Nomoto et al.

(10) Patent No.: US 6,916,861 B2
(45) Date of Patent: Jul. 12, 2005

(54) PIGMENT CONTAINING INK AND PRODUCTION METHOD THEREOF

(75) Inventors: Tsuyoshi Nomoto, Tokyo (JP); Tetsuya Yano, Kanagawa (JP); Shinya Kozaki, Tokyo (JP); Tsutomu Honma, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 306 days.

(21) Appl. No.: 10/133,402

(22) Filed: Apr. 29, 2002

(65) Prior Publication Data

US 2003/0203987 A1 Oct. 30, 2003

(30) Foreign Application Priority Data

Apr. 27, 2001 (JP) .......................................... 2001/133550
Jul. 10, 2001 (JP) .......................................... 2001/210050

(51) Int. Cl.$^7$ .............................. C12N 7/62; C03G 9/00; C03G 17/00; C09D 11/00
(52) U.S. Cl. .................... 523/160; 435/135; 428/32.36; 428/327; 428/403; 523/16.1; 524/538; 524/542
(58) Field of Search ................................ 428/327, 403, 428/32.36; 524/542, 538; 435/135; 523/160, 161

(56) References Cited

U.S. PATENT DOCUMENTS

| | | | |
|---|---|---|---|
| 4,665,107 A | | 5/1987 | Micale ........................ 523/105 |
| 4,692,188 A | | 9/1987 | Ober et al. .................... 106/23 |
| 5,004,664 A | * | 4/1991 | Fuller et al. .............. 430/109.4 |
| 5,085,698 A | | 2/1992 | Ma et al. ...................... 106/20 |
| 5,533,175 A | * | 7/1996 | Lung et al. .................. 358/1.16 |
| 5,543,219 A | | 8/1996 | Elwakil .................. 428/402.24 |
| 5,989,701 A | * | 11/1999 | Goetzen et al. ............. 428/327 |

FOREIGN PATENT DOCUMENTS

| | | |
|---|---|---|
| EP | 0 861 880 | 9/1998 |
| EP | 1 275 728 | 1/2003 |
| EP | 1 321 495 | 6/2003 |
| JP | 58-45272 | 3/1983 |
| JP | 62-95366 | 5/1987 |
| JP | 62-254833 | 11/1987 |
| JP | 07 070494 | 3/1995 |
| JP | 10-140065 | 5/1998 |
| JP | 2000-290573 | 10/2000 |
| JP | 2001-69968 | 3/2001 |
| JP | 2001-78753 | 3/2001 |
| WO | WO 00/24503 | 5/2000 |

OTHER PUBLICATIONS

Rehm, et al.; "A New Metabolic Link . . . Synthesis"; J. Biol. Chem., 273, 37, 24044–24051 (1998).
Vogel, et al.; "Acetylornithinase of *Escherichia coli* . . . Properties"; J. Biol. Chem., 218, 97–106 (1956).
Speier, et al.; "The Addition of Silicon Hydrides to Olefinic Double Bonds . . . Tribromosilane"; J.A.C.S. 78, 2278 (1956).
Kraak, et al.; "In vitro activities of granule–bound poly [(R)–3–hyroxyalkanoate] . . . *oleovorans*" Eur. J. Biochem; 250, 432–439, 1997.
Fritzsche, et al.; "Production of unsaturated polyesters . . . *oleovorans*"; Int. J. Biol. Macromol., 1990, 12, 85–91.
Gerngross, et al.; "Enzyme–catalyzed . . . in vitro"; Proc. Natl. Acad. Sci. USA, 92, 6279–6283, 1995.
Jossek, et al.; "In vitro synthesis of . . . recycling system"; FEMS Microbiology Letters 168, (1998) 319–324.
Lenz, et al.; "Extracellular polymerization . . . *eutrophus*"; International Journal of Biological Macromolecules 25, (1999) 55–60.
Nobes, et al.; "Growth and kinetics of in vitro poly([R]–(—)– 3–hydroxybutyrate) . . . coalescence"; Macromol. Rapid Commun. 21, 77–84 (2000).
Steinbüchel, et al.; "In vitro synthesis of poly(3–hydroxydecanoate) . . . *aeruginosa*"; Appl. Microbiol. Biotechnol. (2000) 54: 37–43.
Pelletier, et al.; 2–Hydroxycyclohexanecarboxyl Coenzyme . . . *palustris*; J. Bact. 182, 10, 2753–2760 (2000).

* cited by examiner

*Primary Examiner*—Herbert J. Lilling
(74) *Attorney, Agent, or Firm*—Fitzpatrick, Cella, Harper & Scinto

(57) ABSTRACT

A micro-capsulated pigment containing pigment ink being excellent in density, fineness, transparency, and coloring and color rendering properties required for ink solutions and having excellent dispersibility and dispersion stability with time due to the reduced particle size is provided. At least a color material with at least part of the surfaces of pigment particles covered with polyhydroxyalkanoate, and a medium for dispersion of the color material are used to obtain the pigment ink.

52 Claims, 3 Drawing Sheets

PIGMENT CONTAINING INK AND PRODUCTION METHOD THEREOF

BACKGROUND OF THE INVENTION

1. Field of the Invention

The present invention relates to a pigment ink having excellent dispersibility for an aqueous or oil medium and excellent dispersion stability with time, which can be used as either an water-based or oil-based pigment ink, and a process for production of the same.

2. Related Background Art

Printing inks and paints include dye based inks with dyes dissolved in solvents as colorants, and pigment based inks with solid pigments dispersed in liquid as colorants. The pigment based ink generally has an advantage that the ink is not fading, can retain a fast color, and is excellent in brightness, but also has a disadvantage that the ink tends to coagulate in long-term storage and high-temperature storage, thus rising a problem in terms of storage stability.

Hitherto, there have been many technical commentaries for production of inks from pigments, namely processes for production of inks, and dispersion of pigment is defined as a process including three steps of wetting-dispersion-stabilization. (General guidebooks include "Latest Dispersion Technology" by Gijutu Joho Kyokai Co., Ltd., issued in Jan. 16, 1993.) A various kinds of resin solution grade water-based pigment inks each using a water soluble resin as a binder and dispersant for stably dispersing the pigment in water have been proposed (Japanese Patent Application Laid-Open Nos. 58-45272, 62-95366, 62-254833, etc.). In addition, in Japanese Patent Application Laid-Open No. 10-140065, an anionic micro-capsulated pigment with a pigment covered with an organic polymer containing an anionic group is proposed. In addition, in U.S. Pat. No. 5,085,698 is disclosed a method in which an AB or BAB block copolymer having a hydrophilic segment and a segments bound to the pigment is used to provide storage stability.

An oil-based pigment ink using as a dispersant a polymer mutually soluble with a solvent to be used for stably dispersing a pigment in the solvent has been proposed (Japanese Patent Application Laid-Open No. 2000-290573).

Some of pigment inks containing conventional micro-capsulated pigments have a disadvantage that transparency, chromophoric properties, color rendering properties and the like may be degraded because dispersion of the micro-capsulated pigment is unstable and thus coagulation tends to occur, and because of large particle sizes. In addition, if the concentration of resin in the capsule is increased (the concentration of pigment is decreased), selectivity of the material for use in the ink is lowered, flexibility is compromised, and the recording liquid becomes lacking in density. In addition, if the concentration of pigment is excessively increased, it becomes difficult to produce a fine micro-capsulated pigment using resin alone, and therefore enormous manpower, equipment, energy, etc. are required, or a large amount of surfactant must be used in combination, and thus an ink record image having a satisfactory water resisting property can not always be obtained.

For the problems to be solved by the invention, the invention has as its object provision of a micro-capsulated pigment containing pigment ink being excellent in density, fineness, transparency, coloring and color-rendering properties and the like due to reduced particle size, and having excellent dispersibility and dispersion stability with time.

Another object of the present invention is to provide a micro-capsulated pigment containing water-based ink or oil-based ink excellent in freedom in selectivity of resin for inks, various kinds of additives, solvents or the like.

Still another object of the present invention is to provide a micro-capsulated pigment containing water-based ink or oil-based ink capable of achieving reduction of labor in the step of finely dispersing a micro-capsulated pigment in a dispersion medium in an ink composition, saving on enormous manpower, equipment, energy and the like, and reducing costs for producing the ink, and a process for production the same.

SUMMARY OF THE INVENTION

As a result of vigorous studies conducted by the inventors in order to solve the above problems, it has been found that it is possible for the pigment to be contained in a fine microcapsule easily without using a surfactant by fixing a polyhydroxyalkanoate (hereinafter referred to as PHA if abbreviated) synthetizing enzyme to a pigment dispersed in an aqueous medium and adding 3-hydroxyacyl CoA thereto to carry out a reaction, and at this time, the pigment is contained in high density because the surface of the pigment is covered directly with the PHA, and PHA constituting the shell of the micro-capsulated pigment can be optionally set to a composition having hydrophilic or lipophilic nature or other natures by selection of an appropriate type of 3-hydroxyacyl CoA. In addition, it has been found that a micro-capsulated pigment with various kinds of properties and the like improved can be obtained by subjecting the PHA to chemical modification. Further specifically, it has been found that by introducing a graft chain into the PHA, for example, it is possible to obtain a micro-capsulated pigment with at least part of the pigment covered by PHA having various kinds of properties derived from the graft chain. In addition, it has been found that by cross-linking the PHA, it is possible to obtain a micro-capsulated pigment with at least part of the pigment covered with PHA having desired physicochemical properties (e.g. mechanical strength, chemical resistance, heat resistance, etc.) Furthermore, the term "chemical modification" in the present invention means carrying out an intramolecular or intermolecular chemical reaction of a polymer material, or carrying out a chemical reaction between a polymer material and another chemical to modify the molecular structure of the polymer material. The term "crosslinking" means chemically or physicochemically making an intramolecular or intermolecular linkage of a polymer material to form a network structure, and the term "crosslinking agent" means a substance having certain reactivity with the above described polymer material that is added for carrying out the above described crosslinking reaction.

Then, it has been found that the micro-capsulated pigment exhibits satisfactory dispersibility in the absence of surfactant in water-based, oil-based and both water and oil-based compositions by appropriately selecting the composition of PHA, and that due to the reduced particle size, the micro-capsulated pigment is excellent in density, fineness, transparency, coloring and color rendering properties, and has excellent dispersibility and dispersion stability with time, leading to completion of the present invention.

According to an aspect of the present invention, there is provided a pigment ink containing a color material with at least a part of surfaces of pigment particles covered with polyhydroxyalkanoate, and a medium for dispersion of the color material.

According to another aspect of the present invention, there is provided a process for preparing a pigment ink containing a color material and a medium for dispersion of the color material, comprising the steps of carrying out a polyhydroxyalkanoate synthesis reaction with 3-hydroxyarcyl CoA as a substrate in the presence of a polyhydroxyalkanoate synthesizing enzyme fixed on the surfaces of pigment particles dispersed in an aqueous medium, thereby at least a part of the surface of the pigment particle is covered with polyhydroxyalkanoate to obtain the color material, and dispersing the color material in the medium for dispersion.

The color material in the present invention has a structure in which at least part of the surface of the pigment particle is covered with polyhydroxyalkanoate, and it is not necessarily required that the entire surface be covered as long as desired properties of color material can be obtained. In a state in which the entire surface is covered, a microcapsulated pigment as color material with the pigment particle as a core and with a cover of polyhydroxyalkanoate as a shell can be obtained.

DESCRIPTION OF THE PREFERRED EMBODIMENTS

Figure 1A:
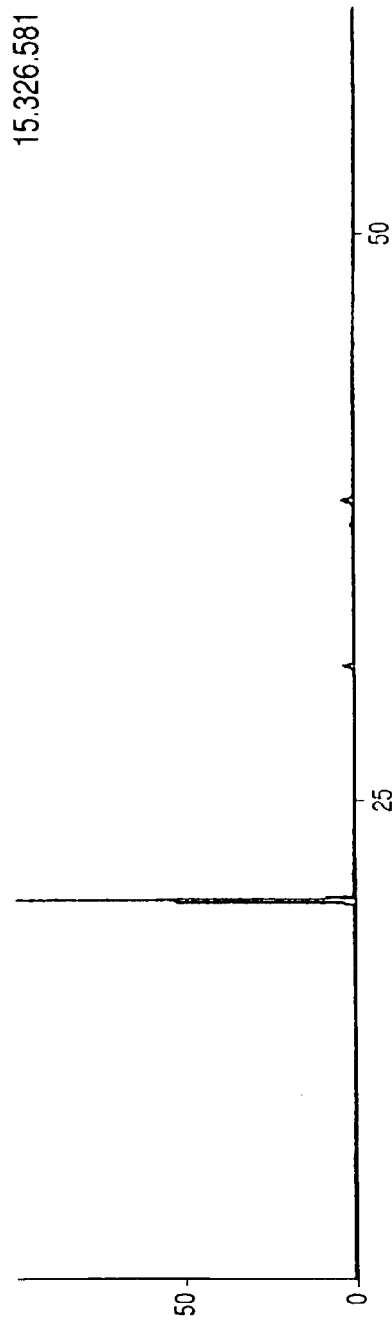
FIGS. 1A and 1B show the results of GC-MS analyses of shells of pigment dispersions of Example 1.

The present invention will be described more in detail below.

<PHA>

PHA capable of being used in the present invention is not particularly limited as long as such a PHA can be synthesized with a PHA synthesizing enzyme involved in a biosynthesis reaction of PHA.

Here, the biosynthesis of PHA is carried out through a polymerization reaction by an enzyme using as a substrate (R)-3-hydroxyacyl CoA produced from alkanoic acids as a substrate by way of various metabolic pathways in an organism (e.g. β-oxidation system and fatty acid synthesis pathway). It is a PHA synthesizing enzyme (also referred to as PHA polymerase, PHA synthase) that catalyses this polymerization reaction. The term "CoA" is an abbreviation of coenzyme A, of which chemical structure is as follows:

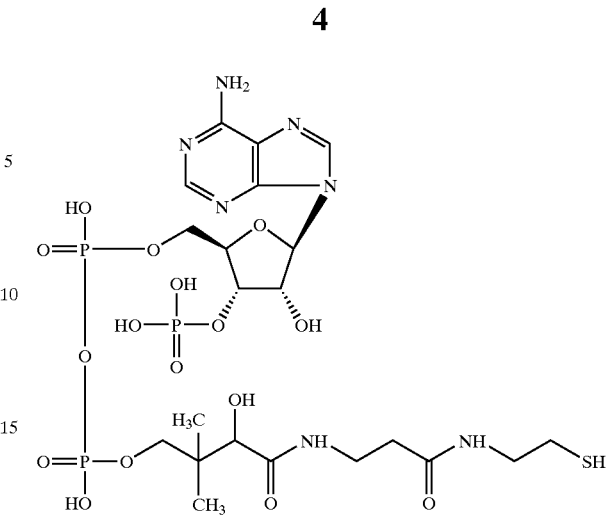

A reaction by which PHA is produced from alkanoic acid through a polymerization reaction by a β-oxidation system and a PHA synthesizing enzyme is shown in the following:

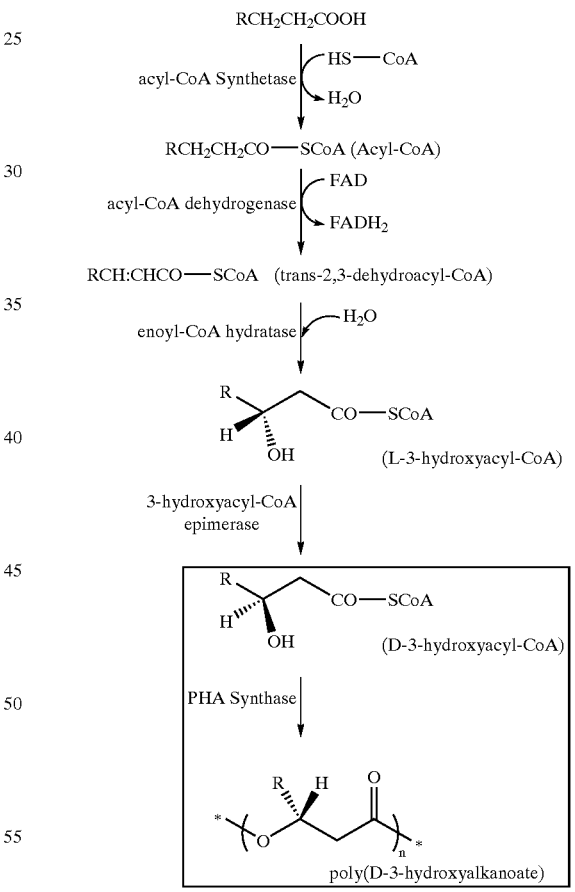

On the other hand, if the reaction is carried out by way of the fatty acid synthesis pathway, it can be considered that PHA is similarly synthesized by the PHA synthesizing enzyme using as a substrate (R)-3-hydroxyacyl CoA into which (R)-3-hydroxyacyl-ACP (ACP means an acyl carrier protein) produced in the pathway has been converted.

In addition, it is known that the above described PHB synthesizing enzyme and PHA synthesizing enzyme can be taken out from the cell to synthesize PHA in a cell-free system (in vitro), and specific examples thereof will be described below.

For example, in Proc. Natl. Acad. Sci. USA, 92, 6279–6283 (1995), it is reported that PHB comprising a 3-hydroxy-n-butanoic acid unit has been successfully synthesized by making 3-hydroxybutyryl CoA act on a PHB synthesizing enzyme derived from *Alcaligenes eutrophus*. In addition, it is reported in Int. J. Biol. Macromol., 25, 55–60 (1999) that PHA comprising a 3-hydroxy-n-butyryl acid unit or a 3-hydroxy-n-valeric acid unit has been successfully synthesized by making 3-hydroxybutyryl CoA and 3-hydroxyvaleryl CoA act on the PHB synthesizing enzyme derived from *Alcaligenes eutrophus*. In addition, according to this report, when racemic 3-hydroxybutyryl CoA was made to act on the enzyme, PHB comprising only a 3-hydroxy-n-butyric acid unit of R-configuration was synthesized due to the stereoselectivity of the enzyme. Synthesis of PHB outside the cell using a PHB synthesizing enzyme derived from *Alcaligenes eutrophus* is also reported in Macromol. Rapid Commun., 21, 77–84 (2000). In addition, it is reported in FEMS Microbiol. Lett., 168, 319–324 (1998) that PHB comprising a 3-hydroxy-n-butyric unit has been successfully synthesized by making 3-hydrozybutyryl CoA act on a PHB synthesizing enzyme derived from *Chromatium vinosum*. It is reported in Appl. Microbiol. Biotechnol., 54, 37–43 (2000) that PHA comprising a 3-hydroxydecanoic acid unit has been synthesized by making 3-hydroxydecanoyl CoA act on a PHA synthesizing enzyme from *Pseudomonas aeruginosa*.

In this way, the PHA synthesizing enzyme is an enzyme catalyzing a final stage in the PHA synthesis reaction system in an organism, and any PHA known to be capable of being synthesized in the organism is synthesized under catalytic action by the enzyme. Therefore, by making 3-hydroxyacyl CoA corresponding to desired PHA act on the enzyme fixed on the medium in the present invention, micro-capsulated pigments with the pigments covered with any type of PHA known to be capable of being synthesized in the organism can be prepared.

As an example of PHA for use in the present invention, PHA containing at least monomer units expressed by the following formulas [1] to [10] can specifically be shown.

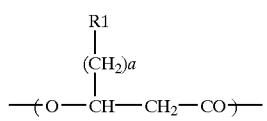
[1]

(wherein the monomer unit is at least one selected from the group consisting of monomer units having any of the following combinations of R1 and a:

a monomer unit in which R1 represents a hydrogen atom (H), and a represents an integer number of 0 to 10;

a monomer unit in which R1 represents a halogen atom, and a represents an integer number of 1 to 10;

a monomer unit in which R1 represents a chromophoric group, and a represents an integer number of 1 to 10;

a monomer unit in which R1 represents a carboxyl group or a salt thereof, and a represents an integer number of 1 to 10; and a monomer unit in which R1 represents

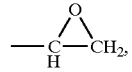

and a represents an integer number of 1 to 7.)

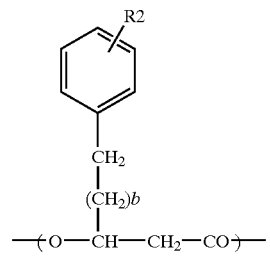
[2]

(wherein b represents an integer number of 0 to 7, and R2 represents any one selected from the group consisting of a hydrogen atom (H), halogen atom, —CN, —NO$_2$, —CF$_3$, —C$_2$F$_5$ and —C$_3$F$_7$.)

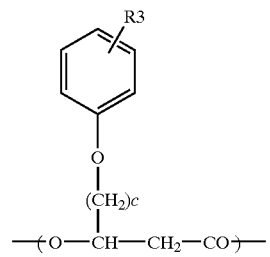
[3]

(wherein c represents an integer number of 1 to 8, and R3 represents any one selected from the group consisting of a hydrogen atom (H), halogen atom, —CN, —NO$_2$, —CF$_3$, —C$_2$F$_5$ and —C$_3$F$_7$.)

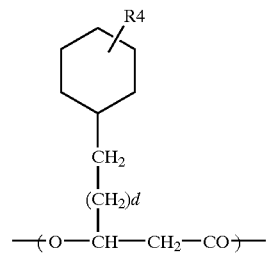
[4]

(wherein d represents an integer number of 0 to 7, and R4 represents any one selected from the group consisting of a hydrogen atom (H), halogen atom, —CN, —NO$_2$, —CF$_3$, —C$_2$F$_5$ and —C$_3$F$_7$.)

[5]

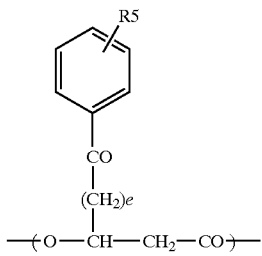

(wherein e represents an integer number of 1 to 8, and R5 represents any one selected from the group consisting of a hydrogen atom (H), halogen atom, —CN, —NO$_2$, —CF$_3$, —C$_2$F$_5$, —C$_3$F$_7$, —CH$_3$, —C$_2$H$_5$ and —C$_3$H$_7$).

[6]

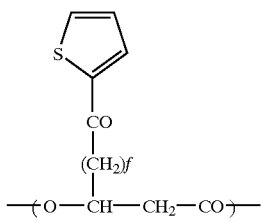

(wherein f represents an integer number of 0 to 7.)

[7]

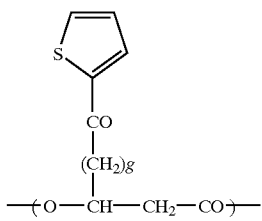

(wherein g represents an integer number of 1 to 8.)

[8]

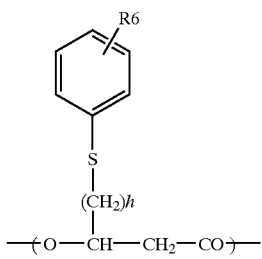

(wherein h represents an integer number of 1 to 7, R6 represents any one selected from the group consisting of a hydrogen atom (H), halogen atom, —CN, —NO$_2$, —COOR', —SO$_2$R", —CH$_3$, —C$_2$H$_5$, —C$_3$H$_7$, —CH(CH$_3$)$_2$ and —C(CH$_3$)$_3$ wherein R' represents any of a hydrogen atom (H), Na, K, —CH$_3$ and —C$_2$H$_5$, and R" represents any of —OH, —ONa, —OK, a halogen atom, —OCH$_3$ and —OC$_2$H$_5$.)

[9]

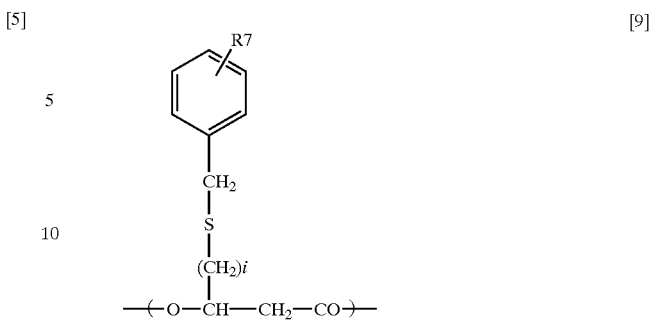

(wherein i represents an integer number of 1 to 7, R7 represents any one selected from the group consisting of a hydrogen atom (H), halogen atom, —CN, —NO$_2$, —COOR' and —SO$_2$R" wherein R' represents any of a hydrogen atom (H), Na, K, —CH$_3$ and —C$_2$H$_5$, and R" represents any of —OH, —ONa, —OK, a halogen atom, —OCH$_3$ and —OC$_2$H$_5$.)

[10]

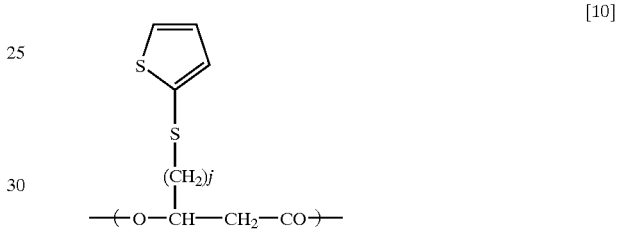

(wherein j represents an integer number of 1 to 9.)

Furthermore, examples of the above described halogen atom may include fluorine, chlorine and bromine.

A specific example of 3-hydroxyacyl CoA for use as a substrate for synthesizing the above PHA may be 3-hydroxyacyl CoA expressed by the following Chemical Formulas [12] to [21]:

[12]

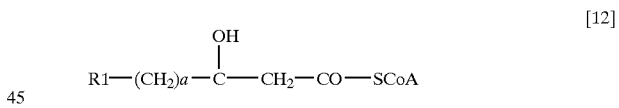

(wherein —SCoA represents a CoA bound to alkanoic acid, and the combination of R1 and a is at least one selected from the group consisting of the following no combinations, and corresponds to the R1 and a in the monomer unit expressed by the above described Formula [1]:

a monomer unit in which R1 represents a hydrogen atom (H), and a represents an integer number of 0 to 10;

a monomer unit in which R1 represents a halogen atom, and a represents an integer number of 1 to 10;

a monomer unit in which R1 represents a chromophoric group, and a represents an integer number of 1 to 10;

a monomer unit in which R1 represents a carboxyl group or a salt thereof, and a represents an integer number of 1 to 10; and a monomer unit in which R1 represents

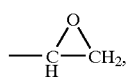

[13]

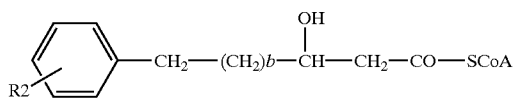

(wherein —SCoA represents a CoA bound to alkanoic acid, b represents any one of integer numbers of 0 to 7 corresponding to b in the monomer unit expressed by the above described Chemical Formula [2], and R2 represents any one selected from the group consisting of a hydrogen atom (H), halogen atom, —CN, —$NO_2$, —$CF_3$, —$C_2F_5$ and —$C_3F_7$ corresponding to R2 in the monomer unit expressed by the above described Chemical Formula [2].)

[14]

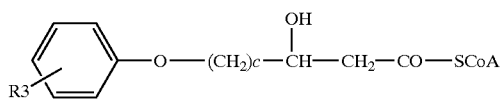

(wherein —SCoA represents a CoA bound to alkanoic acid, c represents any one of integer numbers of 1 to 8 corresponding to c in the monomer unit expressed by the above described Chemical Formula [3], and R3 represents any one selected from the group consisting of a hydrogen atom (H), halogen atom, —CN, —$NO_2$, —$CF_3$, —$C_2F_5$ and —$C_3F_7$ corresponding to R3 in the monomer unit expressed by the above described Chemical Formula [3].)

[15]

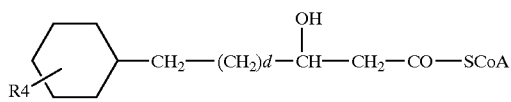

(wherein —SCoA represents a CoA bound to alkanoic acid, d represents any one of integer numbers of 0 to 7 corresponding to d in the monomer unit expressed by the above described Chemical Formula [4], and R4 represents any one selected from the group consisting of a hydrogen atom (H), halogen atom, —CN, —$NO_2$, —$CF_3$, —$C_2F_5$ and —$C_3F_7$ corresponding to R4 in the monomer unit expressed by the above described Chemical Formula [4].)

[16]

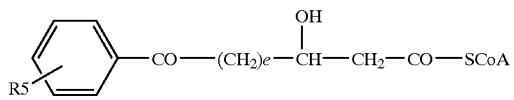

(wherein —SCoA represents a CoA bound to alkanoic acid, e represents any one of integer numbers of 1 to 8 corresponding to e in the monomer unit expressed by the above described Chemical Formula [5], and R5 represents any one selected from the group consisting of a hydrogen atom (H), halogen atom, —CN, —$NO_2$, —$CF_3$, —$C_2F_5$, —$C_3F_7$, —$CH_3$, —$C_2H_5$ and —$C_3H_7$ corresponding to R4 in the monomer unit expressed by the above described Chemical Formula [5])

[17]

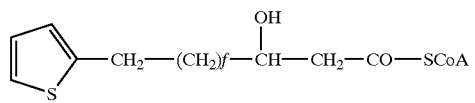

(wherein —SCoA represents a CoA bound to alkanoic acid, and f represents any one of integer numbers of 0 to 7 corresponding to f in the monomer unit expressed by the above described Chemical Formula [6].)

[18]

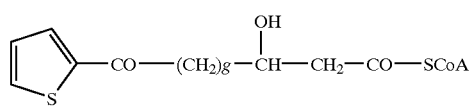

(wherein —SCoA represents a CoA bound to alkanoic acid, and g represents any one of integer numbers of 1 to 8 corresponding to g in the monomer unit expressed by the above described Chemical Formula [7].)

[19]

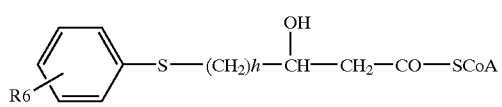

(wherein —SCoA represents a CoA bound to alkanoic acid, h represents any one of integer numbers of 1 to 7 corresponding to h in the monomer unit expressed by the above described Chemical Formula [8], and R6 represents any one selected from the group consisting of a hydrogen atom (H), halogen atom, —CN, —$NO_2$, —COOR', —$SO_2$R", —$CH_3$, —$C_2H_5$, —$C_3H_7$, —$CH(CH_3)_2$ and —$C(CH_3)_3$ corresponding to R6 in the monomer unit expressed by the above described Chemical Formula [8] wherein R' represents any of a hydrogen atom (H), Na, K, —$CH_3$ and —$C_2H_5$, and R" represents any of —OH, —ONa, —OK, a halogen atom, —$OCH_3$ and —$OC_2H_5$.)

[20]

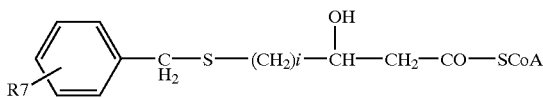

(wherein —SCoA represents a CoA bound to alkanoic acid, i represents any one of integer numbers of 1 to 7 corresponding to i in the monomer unit expressed by the above described Chemical Formula [9], and R7 represents any one selected from the group consisting of a hydrogen atom (H), halogen atom, —CN, —$NO_2$, —COOR' and —$SO_2$R" corresponding to R7 in the monomer unit expressed by the above described Chemical Formula [9] wherein R' represents any of a hydrogen atom (H), Na, K, —$CH_3$ and —$C_2H_5$, and R" represents any of —OH, —ONa, —OK, a halogen atom, —$OCH_3$ and —$OC_2H_5$.)

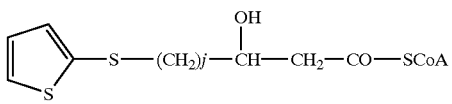

[21]

(wherein —SCoA represents a CoA bound to alkanoic acid, and j represents any one of integer numbers of 1 to 9 corresponding to j in the monomer unit expressed by the above described Chemical Formula [10].)

In addition, in the case where the micro-capsulated pigment of the present invention is used in a water-based pigment ink, PHA having a hydrophilic functional group is used as PHA constituting the micro-capsulated pigment. The hydrophilic functional group may be any hydrophilic functional group, but an anionic functional group can be used, and the anionic functional group may be any anionic functional group, but a carboxyl group can be used in particular. An example of PHA having a carboxyl group may be PHA containing the monomer unit expressed by the following formula [11].

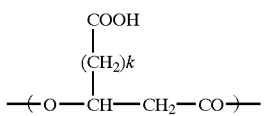

[11]

(wherein the monomer unit is a monomer unit with k representing any one of integer numbers of 1 to 10.)

In addition, a specific example of the above PHA may be PHA containing 3-hydroxypimelic acid expressed by the following Formula [23].

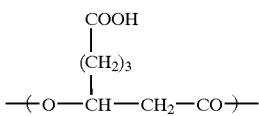

[23]

In addition, an example of 3-hydroxyacyl CoA for use as a substrate for synthesizing PHA expressed by the above Formula [11] may be 3-hydroxyacyl CoA expressed by the following Formula [22].

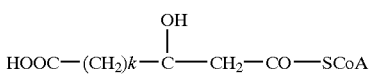

[22]

(wherein SCoA represents a CoA bound to alkanoic acid, and k represents at least one selected from the group consisting of the following numbers, and corresponds to k in the monomer unit expressed by the above described Formula [11]. K represents any one of integer numbers of 1 to 10.)

In addition, 3-hydroxyacyl CoA for use as a substrate for synthesizing PHA containing 3-hydroxypimelic acid expressed by the above Formula [23] may be 3-hydroxypimeril CoA expressed by the following Formula [24].

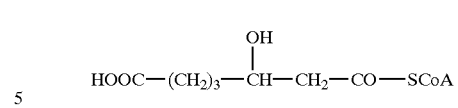

[24]

Furthermore, specific examples of the above described halogen atom may include fluorine, chlorine and bromine. In addition, the above described chromophoric group is not particularly limited as long as its 3-hydroxyacyl CoA body can be subjected to catalytic action of the PHA synthesizing enzyme, but it is more desirable that a methylene chain having 1 to 5 carbon atoms exists between the carboxyl group with CoA bound thereto and the chromophoric group in the 3-hydroxyacyl CoA molecule if considering steric hindrance that may occur during synthesis of a polymer. In addition, if the optical absorption wavelength of the chromophoric group is in the visible range, a colored micro-capsulated pigment can be obtained even if an extender pigment is used. Examples of such chromophoric groups may include nitroso, nitro, azo, diarylmethane, triarylmethane, xanthene, acridine, quinoline, methine, thiazole, indamine, indophenol, lactone, aminoketone, hydroxyketone, stilbene, azine, oxazine, thiazin, anthraquinone, phthalocyanine and indigoid.

For PHA to be used in the present invention, random copolymers and block copolymers each including the above described plurality of monomer units can also be used, thus making it possible to control properties of PHA and provide a plurality of functions using the properties of respective monomer units and contained functional groups, to realize new functions using interaction between functional groups, and so on. In addition, it is also possible to synthesize a block copolymer of any order and composition on the surface of the pigment by selecting as appropriate the amount and order in which 3-hydroxyacyl CoA as a substrate is added. In addition, as required, chemical modification and the like may also be made after or during synthesis of PHA.

It is also possible to change the composition of the monomer unit of PHA in the direction extending from the inside of the pigment to the outside thereof by changing with time the composition such as type and concentration of 3-hydroxyacyl CoA as a substrate, for example. Thereby, for example, if it is necessary to form a cover structure with PHA having a low affinity for the pigment, the substrate is first covered with PHA having a high affinity for the substrate, and the composition of the monomer unit of PHA having a high affinity for the pigment is changed to the composition of the monomer unit of desired PHA in the direction extending from the inside toward the outside, or in the vertical direction to form, for example, a multi-layer structure or gradient structure, thereby making it possible to form a PHA cover with its bonding to the pigment enhanced.

In addition, by introducing a graft chain in PHA on the surface of the micro-capsulated pigment, a micro-capsulated pigment having properties derived from the graft chain can be obtained. In addition, by having PHA on the surface of the pigment crosslinked, a micro-capsulated pigment having excellent mechanical strength can be obtained.

Furthermore, PHA synthesized by a PHA synthesizing enzyme, which is used in the structure of the present invention, is generally an isotactic polymer constituted only by a R-configuration.

3-hydroxyacyl CoA as a synthesis substrate for PHA can be synthesized for use by a method appropriately selected from an in vitro synthesis method using enzymes, an in vivo synthesis method using organisms such as microorganisms and plants, a chemical synthesis method, and the like. In particular, the enzyme synthesis method is a method that is generally used for synthesis of the substrate, and known enzyme synthesis methods include a method using the following reaction using commercially available acyl CoA synthetase (Acyl CoA Ligase, E.C.6.2.1.3)(Eur. J.Biochem., 250, 432–439 (1997), Appl. Microbiol. Biotechnol., 54, 37–43 (2000), etc.):

acyl CoA synthetase 3-hydroxyalkanoic acid+CoA→3-hydroxyacyl CoA.

For the synthesis process using enzymes and organisms, a batch type synthesis method may be used, or series production may be carried out using immobilized enzymes and immobilized cells.

<PHA Synthesizing Enzymes and Microorganisms for Producing the Enzymes>

For the PHA synthesizing enzyme for use in the present invention, an enzyme produced by a microorganism appropriately selected from microorganisms capable of producing the enzyme, or a transformant with the gene of a PHA synthesizing enzyme introduced may be used.

For microorganisms for producing PHA synthesizing enzymes, PHB or PHB/V producing microorganisms may be used, and as these microorganisms, *Burkholderia cepacia* KK01, *Ralstonia eutropha* TB64, *Alcaligenes* sp. TL2 that have been isolated by the inventors may be used in addition to *Aeromonas* sp., *Alcaligenes* sp., *Chromatium* sp., *Comamonas* sp., *Methylobacterium* sp., *Paracoccus* sp., *Pseudomonas* sp. and the like. Furthermore, KK01, TB64 and TL2 are deposited as FERM BP-4235, FERM BP-6933 and FERM BP-6913, respectively, in National Institute of Advanced Industrial Science and Technology, International Patent Organism Depositary.

Also, as microorganisms for producing PHA synthesizing enzymes, microorganisms producing mcl-PHA and unusual-PHA may be used, and as these microorganisms may be used *Pseudomonas* sp. microorganisms such as *Pseudomonas putida* P91, *Psuedomonas cichorii* H45, *Pseudomonas cichorii* YN2, *Pseudomonas jessenii* P161, etc. that have been isolated by the inventors, in addition to *Pseudomonas oleoborans, Pseudomonas resinoborans, Pseudomonas* sp. 61–3, *Pseudomonas putida* KT2442, *Pseudomonas aeruginosa* and the like, and *Burkholderia* sp. microorganisms such as *Burkholderia* sp. OK3 (FERM P-17370) described in Japanese Patent Application Laid-Open No. 2001-78753 and *Burkholderia* sp. OK4 (FERM P-17371) described in Japanese Patent Application Laid-Open No. 2001-69968. Also, in addition to these microorganisms, microorganisms belonging to *Aeromonas* sp., *Comamonas* sp. and the like and producing mcl-PHA and unusual-PHA can be used.

Furthermore, P91, H45, YN2 and P161 are deposited on an international basis as FERM BP-7373, FERM BP-7374, FERM BP-7375 and BP-7376, respectively, in National Institute of Advanced Industrial Science and Technology, International Patent Organism Depositary, under Budapest Treaty on international approval for deposition of microorganisms in terms of patent procedures.

For normal culture of microorganisms for use in production of PHA synthesizing enzymes according to the present invention, for example preparation of stock strains, and reproduction for securing the number of cells and their active states required for production of the PHA synthesizing enzyme, a culture medium containing components needed for growth of microorganisms to be used is appropriately selected and used. For example, any type of culture media such as general natural culture media (broths, yeast extracts, etc) and synthetic culture media with nutrient sources added thereto may be used unless they adversely affect growth and survival of microorganisms.

For the culture, any method such as liquid culture and solid culture may be used as long as reproduction of the microorganisms is possible. In addition, any type of culture including batch culture, fed batch culture, semi-continuous culture and continuous culture may be used. As for the form of the liquid batch culture, a method in which oxygen is supplied by shaking with a shaking flask, a method in which oxygen is supplied using a stirring aeration system with a jar fermenter and the like are employed. In addition, a multi-stage method in which these steps are connected in multiple stages may be employed.

In the case where the PHA synthesizing enzyme is produced using PHA producing microorganisms as described above, for example, a method in which the microorganism is grown in an inorganic culture medium containing alkanoic acid such as octanoic acid and nonanoic acid, and cells of the microorganism in the logarithmic growth phase to the early stage of the stationary phase are collected by centrifugation or the like to extract a desired enzyme, and so on may be used. Furthermore, if the microorganism is cultured using a condition as described above, mcl-PHA derived from added alkanoic acid is synthesized in a cell of the microorganism, but in this case, it is generally said that the PHA synthesizing enzyme exists in such a manner as to be bound to small particles of PHA produced in the cell. However, as a result of studies conducted by the inventors, it has been found that almost equivalent enzyme activity is present even in the supernatant liquid after conducting centrifugation of the liquid from fragmentation of cells cultured by any of the above described methods. It is assumed that this is because an almost equivalent amount of PHA synthesizing enzyme exists in a free state in a relatively early stage of culture, which is from the logarithmic growth phase to the early stage of the stationary phase as described above, since the enzyme is actively produced continuously in the cell.

For the inorganic culture medium for use in the above culture methods, any medium containing components enabling microorganisms to be grown such as phosphorous sources (e.g. phosphates) and nitrogen sources (e.g. ammonium salts, nitrates, etc.) may be used, and inorganic culture media may include, for example, a MSB medium, E medium (J. Biol. Chem., 218, 97–106 (1956)) and M9 medium. Furthermore, the composition of the M9 medium for use in Examples of the present invention is as follows:

Na$_2$HPO$_4$: 6.2 g
KH$_2$PO$_4$: 3.0 g
NaCl: 0.5 g
NH$_4$Cl: 1.0 g
(per liter of medium, pH 7.0).

In addition, about 0.3% (v/v) of a solution containing minor components shown below is preferably added in the above inorganic culture medium for ensuring satisfactory growth of the microorganism and production of the PHA synthesizing enzyme:

(Solution Containing Minor Components)
nitrilotriacetic acid: 1.5 g
MgSO$_4$: 3.0 g
MnSO$_4$: 0.5 g
NaCl: 1.0 g
FeSO$_4$: 0.1 g
CaCl$_2$: 0.1 g
CoCl$_2$: 0.1 g
ZnSO$_4$: 0.1 g
CuSO$_4$: 0.1 g AlK $(SO_4)_2$: 0.1 g
H$_3$BO$_3$: 0.1 g
Na$_2$MoO$_4$: 0.1 g
NiCl$_2$: 0.1 g
(per liter)

The culture temperature may be any temperature at which the above microorganism can satisfactorily be grown, for example 14 to 40° C., preferably 20 to 35° C.

Also, a desired PHA synthesizing enzyme can be produced using a transformant having a PHA synthesizing enzyme gene of the aforesaid PHA producing microorganism. Cloning of the PHA synthesizing enzyme gene, preparation of an expression vector, and preparation of the transformant may be carried out in accordance with an established method. In a transformant obtained with a microorganism such as colibacillus as a host, the medium for use in culture is a natural medium or a synthetic medium, for example, a LB medium, M9 medium or the like. A culture temperature is in the range of from 25 to 37° C. In addition, aerobic culture is conducted for 8 to 27 hours to achieve growth of the microorganism. Thereafter, cells can be collected to collect the PHA synthesizing enzyme accumulated in the cells. Antibiotics such as kanamycin, ampicillin, tetracycline, chloramphenicol and streptomycin may be added in the medium as necessary. Also, in the case where an inductive promoter is used in the expression vector, an inductive material corresponding to the promoter may be added to the medium to promote expression when the transformant is cultured. Such inductive materials include, for example, isopropyl-1-thio-β-D-galactoside (IPTG), tetracycline and indolacrylic acid (IAA).

For the PHA synthesizing enzyme, liquids from fragmentation of cells of microorganism, and crude enzymes such as salted ammonium sulfate obtained by precipitation and collection of protein components with ammonium sulfate and the like may be used, or enzymes purified by various kinds of methods may be used. Stabilizers such as metal salts, glycerin, dithiothreitol, EDTA and bovine serum albumin (BSA), and activators may be added to the enzymes as necessary.

For isolation and purification of PHA synthesizing enzymes, any method allowing enzyme activation of PHA synthesizing enzymes to be retained may be used. For example, obtained cells of microorganism are crushed with a French press, a supersonic crusher, lysozyme, various kinds of surfactants and the like, and thereafter, for a crude enzyme solution obtained by centrifugation or salted ammonium sulfate prepared therefrom, means such as affinity chromatography, cation or anion exchange chromatography, and gel filtration is applied alone or in combination, whereby a purified enzyme can be obtained. In particular, a gene recombination protein can be purified more conveniently by expressing the protein in the form of united protein with "tags" such as histidine residues bound to the N terminal and C terminal, and making the protein to be bound to an affinity resin through these tags. For isolating a desired protein from the united protein, methods of cleaving the linkage by protease such as thrombin and a blood coagulation factor Xa, decrasing the pH, adding a high concentration of imidazole as a competitive binding agent and the like may be used. Alternatively, if the tag includes intein as in the case of using pTYB1 (manufactured by New EnglanBiolab Co., Ltd.) as a expression vector, a reduction condition is achieved by dithiothreitol or the like to cleave the linkage. For the united protein enabling purification by affinity chromatography, glutathione-S-transferase (GST), chitin bound domain (CBD), maltose bound protein (MBP) and thioredoxine (TRX) are also well known in addition to the histidine tag. The GST united protein can be purified by the GST affinity resin.

A various kinds of reported methods may be used for measuring activity of the PHA synthesizing enzyme, and for example, the activity may be measured by the following method in which as a measurement principle, CoA released in the process through which 3-hydroxyacyl CoA is polymerized under the catalytic action of the PHA synthesizing enzyme to form PHA is colored with 5,5'-dithiobis-(2-nitrobenzoic acid) to carry out measurements. Reagent 1: bovine serum albumin (manufactured by Sigma Co., Ltd.) is dissolved in a 0.1 M Tris hydrochloric buffer (pH 8.0) in the concentration of 3.0 mg/ml, Reagent 2: 3-hydroxyoctanoyl CoA is dissolved in a 0.1 M Tris hydrochloric buffer (pH 8.0) in the concentration of 3.0 mM, Reagent 3: trichloroacetic acid is dissolved in a 0.1 M Tris hydrochloric buffer (pH 8.0) in the concentration of 10 mg/ml, and Reagent 4: 5,5'-dithiobis-(2-nitrobenzoic acid) is dissolved in a 0.1 M Tris hydrochloric buffer (pH 8.0) in the concentration of 2.0 mM. First reaction (PHA synthesis reaction): 100 µl of Reagent 1 is added in 100 µl of sample (enzyme) solution and mixed together, and is pre-incubated at 30° C. for a minute. 100 µl of Reagent 2 is added thereto and mixed together, and is incubated at 30° C. for 1 to 30 minutes, followed by adding thereto Reagent 3 to stop the reaction. Second reaction (reaction of coloring free CoA): the first reaction solution of which reaction has been stopped is subjected to centrifugation (15,000×g, 10 minutes), and 500 µl of Reagent 4 is added in 500 µl of supernatant liquid of this solution, and is incubated at 30° C. for 10 minutes, followed by measuring an absorbance at 412 nm. Calculation of enzyme activity: the amount of enzyme for releasing 1 µmol of CoA per minute is defined as one unit (U).

<Process for Producing Pigment Ink>

One example of process for production of pigment ink containing micro-capsulated pigments of the present invention may be a process comprising at least steps of (1) dispersing pigments on an aqueous medium, (2) fixing a PHA synthesizing enzyme to the dispersed pigment, (3) adding 3-hydroxyacyl CoA as a substrate, (4) carrying out a PHA synthesis reaction and (5) processing the micro-capsulated pigment as an pigment ink.

The step of dispersing the pigment on the aqueous medium is conducted by adding one or more selected pigments in the aqueous medium, and carrying out dispersion processing, followed by classifying the pigment in a desired range of particle size if necessary.

The pigment for use in the present invention may be an organic or inorganic pigment, but is preferably excellent in heat resistance and light resistance. Examples of organic pigments may include azo-based, phthalocyanine-based, benzimidasolone-based, quinacridone-based, isoindolynone-based, pyrathrone-based, dibromanzanthrone-based, indathrone-based, anthrapyrimidine-based, flavathrone-based, perylene-based, perynone-based, quinophtharone-based, phtharone-based, thioindigo-based, indigo-based, dioxazine-based, anthraquinone-based, xanthene-based, methine-based and azomethine-based pigments, and condensation polycyclic pigments including other metal complex pigments. Examples of inorganic pigments may include Milori blue, iron oxide, cobalt purple, manganese purple, ultramarine blue, Prussian blue, cobalt blue, celluriane blue, pyridiane, emerald green and cobalt green, and one or two types thereof are appropriately selected and used. The above pigments may be used after being subjected to a various kinds of well known surface treatments. Examples of surface treatments include surfactant treatment, coupling treatment and pigment derivative treatment.

Dispersion processing may be carried out using a homo mixer, a horizontal mini mil, a ball mil, a roll mil, a sand grinder, a milling machine, a supersonic operation or the like. In addition, the dispersion may be carried out by a method in which mixtures are passed through a large number of nozzles under a hydraulic pressure of at least 1000 psi (about 70.3 kg/cm$^2$) in a liquid jet interaction if chamber.

It is desirable that the pigment is dispersed in a single dispersion state in the range of from 100 nm to 400 nm for the particle size of the dispersed pigment. If the particle size of the dispersed pigment is not fallen in a desired range, classification by filtration and sedimentation processes can be carried out to make an adjustment.

The particle size of the dispersed pigment can be measured by known methods such as an absorbance method, a static light-scattering method, a dynamic light-scattering method and a centrifugal sedimentation method, and for example, an apparatus for measuring particle sizes such as Coulter counter multi-sizer may be used.

The composition of the aqueous medium for synthesis of PHA in this step may be any composition that allows the pigment to be dispersed in a desired state, and does not interfere the subsequent steps of fixing the enzyme to the pigment and carrying out the PHA synthesis reaction, but the composition may be adjusted into a composition allowing the activity of the PHA synthesizing enzyme to be exerted in order to simplify the subsequent steps. As the composition allowing the activity of the PHA enzyme to be exerted, for example, a buffer may be used. For the buffer, general buffers for use in biochemical reactions, for example, acetate buffers, phosphate buffers, potassium phosphate buffers, 3-(N-morpholino) propane sulfonate (MOPS) buffers, N-tris (hydroxymethyl) methyl-3-aminopropane sulfonate (TAPS) buffers, trischloride buffers, glycin buffers, and 2-(cyclohexylamino) ethanesulfonate (CHES) buffers are suitably used. The concentration of the buffer allowing the activity of the PHA synthesizing enzyme to be exerted may be a general concentration, namely in the range of from 5 mM to 1.0 M, but is preferably in the range of from 10 to 200 mM. Also, an adjustment is made so that pH is in the range of from 5.5 to 9.0, preferably from 7.0 to 8.5, but the possibility is not excluded that a pH condition is set in a range other than the above described range depending on the most suitable pH and pH stability of a PHA synthesizing enzyme to be used.

In addition, for maintaining a pigment dispersion condition in the aqueous medium, a suitable surfactant may be added as long as the surfactant has a type and concentration not interfering the subsequent steps, and has a type and concentration not interfering the purpose of the colored composition of the present invention. Examples of the surfactant may include, for example, anionic surfactants such as sodium oleate, sodium dodecylsulfonate, sodium dodecyl sulfate, sodium dodecyl-N-sarcosinate, sodium cholate, sodium deoxycholate and sodium taurodeoxycholate; cationic surfactants such as cetyltrimethylammonium bromide and dodecylpyridinium chloride; ampholytic surfactants such as 3-[(choleamidepropyl) dimethylammonio]-1-propanesulfonic acid (CHAPS), 3-[(3-choleamidepropyl) dimethylammonio]-2-hydroxy-1-propanesulfonic acid (CHAPSO), palmitoyllysolecithin and dodecyl-β-alanine; and nonionic surfactants such as octylglucoside, octylthioglucoside, heptylthioglucoside, decanoyl-N-methylglucamide (MEGA-10), polyoxyethylenedodecylether (Brij, Lubrol), polyoxyethylene-i-octylphenylether (Triton X), polyoxyethylenenonylphenylether (Nonidet P-40, Triton N), polyoxyethylene fatty acid ester (Span) and polyoxyethylenesorbitol ester (Tween).

In addition, for maintaining a pigment dispersion condition in the aqueous medium, a suitable auxiliary solvent may be added as long as the solvent has a type and concentration not interfering the subsequent steps, and has a type and concentration not interfering the purpose of the colored composition of the present invention. For the auxiliary solvent, one or two types of substances selected from, for example, linear aliphatic hydrocarbons such as hexane, and their derivatives such as monovalent alcohols such as methanol and ethanol, polyvalent alcohols such as glycerol, fatty acid ethers and carboxylates may be selected and used.

The step of fixing the PHA synthesizing enzyme to the pigment can be carried out by adding the PHA synthesizing enzyme in the aforesaid pigment dispersion, and subjecting the same to fixation processing. For the fixation processing, any method may be selected from enzyme fixation methods that are normally used as long as the method allows the activity of the enzyme to be retained, and are capable of being applied in desired pigments. For example, these methods may include a covalent binding method, ion absorption method, hydrophobic adsorption method, physical adsorption method, affinity adsorption method, crosslinking method and lattice inclusion method, but fixation methods using ion adsorption and hydrophobic adsorption are particularly convenient.

The enzyme protein such as a PHA synthesizing enzyme is a polypeptide in which a large number of amino acids are bound, and shows properties as an ion absorbent due to amino acids having free ionic groups such as lycine, histidine, arginine, asparaginic acid and glutamic acid, and have properties as a hydrophobic absorbent due to amino acids having free hydrophobic groups such as alanine, valine, leucine, isoleucine, methionine, tryptophane, phenylalanine and proline in terms that it is an organic macromolecule. Thus, the enzyme protein can be more or less adsorbed to a pigment having ionicity or hydrophobicity, or having both ionicity and hydrophobicity.

In the method in which the PHA synthesizing enzyme is fixed mainly by ion adsorption, a pigment expressing ionic functional groups on the surface may be used, and for example inorganic pigments having clay minerals, metal oxides and the like as main components may be used.

Also, in the method in which the PHA synthesizing enzyme is fixed mainly by hydrophobic adsorption, a pigment with having a nonpolar surface may be used, and for example azo pigments having a plurality of aromatic rings, organic pigments such as fused polycyclic phthalocyanine based pigments and anthraquinone based pigments, and inorganic pigments composed of carbon crystals such as carbon black may be used.

Fixation of the PHA synthesizing enzyme to the pigment by the ion adsorption or hydrophobic adsorption method is achieved by mixing the pigment and the PHA synthesizing enzyme together in a predetermined aqueous medium so that a predetermined concentration is obtained. At this time, it is desirable that the reaction vessel is shaken or stirred at a predetermined strength so that the enzyme can be evenly adsorbed to the surface of the pigment.

In the above described fixation processing, it is desirable that the composition of the aqueous medium in which the pigment and the enzyme are mixed together is determined in consideration of changes in positive and negative surface charge, the amount of charge and hydrophobicity of the pigment and PHA synthesizing enzyme due to the pH and salt concentration of the aqueous medium. For example, if the pigment is ion-adsorptive, the amount of charge contributing to adsorption between the pigment and the PHA synthesizing enzyme can be increased by reducing the salt concentration. Also, the opposite charge of the pigment and PHA synthesizing enzyme can be increased by changing pH. If the pigment is principally hydrophobic-adsorptive, hydrophobicities of the pigment and the PHA synthesizing enzyme can be increased by increasing the salt concentration. Also, the electrophoresis and wetting angle are measured in advance to examine charged conditions and hydrophobicity of the pigment and PHA synthesizing enzyme, whereby the composition suitable for adsorption can be determined. In addition, the amount of adsorption between the pigment and the PHA synthesizing enzyme can directly be measured to determine the composition. For measurements of the amount of adsorption, for example, a method may be used in which a solution of PHA synthesizing enzyme of which concentration is known is added in a solution with a pigment dispersed therein to carry out adsorption processing, followed by measuring the concentration of the PHA synthesizing enzyme in the solution and determining the amount of the adsorbed enzyme using a subtraction method.

In the case of a pigment to which the enzyme is hardly fixed by the ion adsorption method and hydrophobic adsorption method, the enzyme may be fixed to the pigment using the covalent binding method by conducting treatments allowing for possibilities of complication of operations and deactivation of the enzyme as necessary. For example, there are a method in which a pigment having aromatic amino groups is diazotized, and the enzyme is diazo-coupled thereto, a method in which a peptide linkage is formed between the pigment having a carboxyl group and amino group and the enzyme, a method in which alkylation is performed between the pigment having a halogen group and the amino group or the like of the enzyme, a method in which crosslinking is made between the amino group of the solid particle and the amino group of the enzyme, a method in which the pigment having a carboxyl group and amino group is reacted with the enzyme in the presence of a compound having an aldehyde group or a ketone group and an isocyanide compound, and a method in which an exchange reaction is carried out between the pigment having a disulfide group and the thiol group of the enzyme.

In addition, the enzyme may be fixed to a pigment with a ligand introduced therein by affinity adsorption. In this case, any substance may be selected as the ligand as long as it enables affinity adsorption while maintaining the activity of the PHA synthesizing enzyme. Also, the enzyme may be fixed by binding a different biopolymer such as a protein to the PHA synthesizing enzyme, and subjecting the bound biopolymer to affinity adsorption. The biopolymer may be bound to the PHA synthesizing enzyme by gene recombination or the like, or by a chemical process. For example, as described later in Examples, glutathione-S-transferase is united to the PHA synthesizing enzyme by transformation, and the united protein is adsorbed by affinity adsorption to sepharose having introduced therein glutathione as a ligand for glutathione-S-transferase, whereby the enzyme can be fixed.

Also, a peptide including amino acid sequences having binding capacity for the pigment can be united to the polyhydroxyalkanoate synthesizing enzyme and exhibited to fix the polyhydroxyalkanoate synthesizing enzyme on the surface of the pigment based on the bonding between the part of peptide corresponding to the amino acid sequence having binding capacity for the pigment and the pigment.

The amino acid sequence having binding capacity for the pigment can be determined by the screening of a random peptide library, for example. In particular, for example, a phage display peptide library prepared by coupling a random synthesis gene to the N-terminal gene of the surface protein of the M13 type phage (e.g. gene III protein) can be suitably used, but in this case, determination of the amino acid sequence having binding capacity for the pigment is carried out in accordance with the following procedure. Specifically, the phage display peptide library is added to the pigment to contact the phage to the pigment, followed by separating bound phages and non-bound phages by washing. The pigment-bound phage is eluted with an acid or the like and neutralized with a buffer solution, and colibacillus is thereafter infected with the phage to amplify the phage. If this screening process is repeated several times, a plurality of clones having binding capacity for a desired pigment are concentrated. Here, for obtaining a single clone, colonies are made on the culture plate with the phage with which colibacillus is infected again. Each single colony is cultured on the liquid culture medium, followed by precipitating and purifying the phage existing in the supernatant liquid of the medium by polyethylene glycol or the like, and analyzing the base sequence, whereby the structure of the peptide can be known.

The amino sequence of the peptide having binding capacity for the pigment, obtained by the above described method, is united to the polyhydroxyalkanoate synthesizing enzyme using a normal gene engineering methodology for use. The peptide having binding capacity for the pigment can be coupled to the N-terminal or C-terminal of the polyhydroxyalkanoate synthesizing enzyme to be expressed. The peptide can also be expressed with an appropriate spacer sequence inserted. The spacer sequence has preferably about 3 to 400 amino acids, and may include any amino acid. Most preferably, the spacer sequence neither prevents the PHA synthesizing enzyme from functioning nor prevents the PHA synthesizing enzyme from being bound to the pigment.

The pigment with the enzyme fixed thereto, prepared by the above described method, may be used directly, but may also be used after being subjected to freeze-drying or the like.

The amount of enzyme fixed to the pigment may be set in the range of from 10 units (U) to 1,000 units (U), desirably from 50 units (U) to 500 units (U) per 1 g of pigment, wherein one unit (U) is defined as the amount of PHA synthesizing enzyme when the amount of CoA released in the reaction through which PHA is synthesized by polymerization of 3-hydroxyacyl CoA equals 1 $\mu$mol per minute.

A time period over which fixation of the enzyme is carried out is desirably 1 minute to 24 hours, more desirably 10 minutes to 1 hour. Standing the sample at rest or leaving it to stand for excessively long time is not preferable because coagulation of pigments and reduction of enzyme activity may be caused.

Also, the enzyme may be fixed to the pigment by adding the pigment directly to the enzyme solution without carrying out the previous step of dispersing the pigment in the aqueous medium, and then dispersing the pigment in the enzyme solution. In this case, electric repulsion and steric hindrance associated with the ionic functional group possessed by the enzyme fixed to the pigment makes it possible to facilitate dispersion of the pigment in the aqueous medium and eliminate necessity to add a surfactant in the aqueous medium or reduce the amount of the surfactant.

The step of adding 3-hydroxyacyl CoA as a substrate is achieved by adding a preserved solution of 3-hydroxyacyl CoA separately prepared to the aqueous dispersion of the pigment with the enzyme fixed thereto in the previous step so that a desired concentration is reached. 3-hydroxyacyl CoA as a substrate is added in final concentrations of generally from 0.1 mM to 1.0 M, desirably from 0.2 mM to 0.2 M, and further preferably 0.2 mM to 1.0 mM.

Also, in the above describe step, the composition such as type and concentration of 3-hydroxyacyl CoA in the aqueous reaction solution is changed with time, thereby making it possible to change the composition of the monomer unit of PHA covering the pigment in the direction extending from the inside toward the outside of the pigment.

The form of this pigment with the monomer unit composition changed may be, for example, a form in which the change of the composition of the PHA cover is continuous, and the pigment is covered with one layer of PHA having a gradient of composition formed in the direction extending from the inside toward the outside. The production method may be, for example, a method in which 3-hydroxyacyl CoA of different composition is added in the reaction solution while synthesizing PHA.

In addition, as another form, there may be a form in which the composition of the PHA cover is changed by stages, and PHA of different compositions covers the pigment in multiple layers. The production method for this form may be a method in which PHA is synthesized with a certain composition of 3-hydroxyacyl CoA, followed by collecting the pigment under preparation from the reaction solution on a temporary basis using centrifugation or the like, and adding thereto a reaction solution of 3-hydroxyacyl CoA of different composition again, and so on.

The step of carrying out a PHA synthesis reaction is carried out by preparing the composition of reaction solution so that a composition allowing activity of the PHA synthesizing enzyme to be exerted can be obtained if the composition of reaction solution has not been prepared till the previous step, and adjusting the reaction temperature and reaction time, in order that a micro-capsulated pigment having a desired shape can be obtained by PHA to be synthesized.

The concentration of the buffer for the reaction solution allowing the activity of the PHA synthesizing enzyme to be exerted may be a general concentration, namely a concentration in the range of from 5 mM to 1.0 M, but is desirably a concentration in the range of from 10 to 200 mM. For pH, an adjustment is made so that the pH is in the range of from 5.5 to 9.0, preferably from 7.0 to 8.5, but the possibility is not excluded that a pH condition is set in a range other than the above described range depending on the most suitable pH and pH stability of a PHA synthesizing enzyme to be used.

The reaction temperature is set as appropriate depending on the property of the PHA synthesizing enzyme to be used, but may be set normally at 4 to 50° C., preferably at 20 to 40° C. However, the possibility is not excluded that a temperature condition is set in a range other than the above described range depending on the most suitable temperature and heat resistance of a PHA synthesizing enzyme to be used.

The reaction time is appropriately selected and set within the range of normally from 1 minute to 24 hours, preferably from 30 minutes to 3 hours depending on stability, etc. of the PHA synthesizing enzyme to be used.

The micro-capsulated pigment is obtained by this step, but the structure of monomer units of PHA constituting the microcapsule can be determined by extracting PHA from the micro-capsulated pigment with chloroform, and thereafter carrying out composition analysis by gas chromatography or the like, or using a time-of-flight secondary ion mass spectrometer (TOF-SIMS) and an ion sputtering technique.

The molecular weight of PHA is not particularly limited, but the molecular weight is desirably in the range of from 1,000 to 10,000,000, more preferably from 3,000 to 1,000,000 for maintaining strength of the micro-capsulated pigment, and providing a stable amount of charge. The molecular weight of PHA may be measured by GPC (gel permeation chromatography) after PHA is extracted from the micro-capsulated pigment with chloroform.

Also, in the method of producing the micro-capsulated pigment according to the present invention, density of the pigment in the microcapsule can be increased because the pigment can be directly covered with PHA. On the other hand, however, it is required that the amount of PHA covering the pigment should be increased to enhance dispersibility and mechanical strength of the micro-capsulated pigment, and consequently, the amount of PHA covering the pigment is, for example, in the range of from 1 to 30% by mass, preferably from 1 to 20% by mass, more preferably 1 to 15% by mass of the weight of the pigment.

The particle size of the micro-capsulated pigment obtained by the above step is 1 μm or smaller, preferably 0.7 μm or smaller, more preferably 0.01 to 0.4 μm. The particle size of the micro-capsulated pigment can be measured by known methods such as an absorbance method, a static light-scattering method, a dynamic light-scattering method and a centrifugal sedimentation method, and for example, an apparatus for measuring particle sizes such as a Coulter counter multi-sizer may be used.

In addition, the micro-capsulated pigment obtained by this step may be subjected to various kinds of secondary treatments and processing such as chemical modification before being used.

For example, a micro-capsulated pigment having further useful functions and properties can be obtained by subjecting PHA on the surface of the pigment to chemical modification. For example, a graft chain is introduced, whereby a micro-capsulated pigment having various kinds of properties derived from the graft chain can be obtained. If polysiloxane as described later is introduced as a graft chain, for example, a micro-capsulated pigment having improved mechanical strength, dispersibility, weather resistance, water repellency (resistance), heat resistance and the like can be obtained, and storage stability and weather resistance of pigment ink using the pigment can be improved. In addition, by having PHA on the surface of the pigment crosslinked, mechanical strength, chemical resistance, heat resistance and the like of the micro-capsulated pigment can be improved.

The method for chemical modification is not particularly limited as long as it is a method by which the purpose of obtaining a desired function and structure is achieved, but, for example, a method in which PHA having a reactive functional group on the side chain is synthesized, and chemical modification is accomplished using the chemical reaction of the functional group may be used as a suitable method.

The type of the above described reactive functional group is not particularly limited as long as it serves the purpose of obtaining a desired function and structure, and may be, for example, an epoxy group as described previously. PHA having an epoxy group on the side chain can be chemically converted as in the case of a normal polymer having an epoxy group. Specifically, for example, conversion into a hydroxyl group, and introduction of a sulfone group are possible. Also, a compound having thiol and amine can be added, and for example, a compound having a reactive functional group at the terminal, specifically a compound having an amino group having high reactivity with the epoxy group is added and reacted, whereby the graft chain of polymer is formed.

Compounds having amino groups on the terminals may include, for example, polyvinyl amine, polyethylene imine, and amino modified polymers such as amino modified polysiloxane (amino modified silicone oil). Among them, for amino modified polysiloxane, commercially available modified silicone oil, or amino modified polysiloxane that is synthesized by a method described in J. Amer. Chem. Soc., 78, 2278 (1956) or the like may be used, and the effect of improving mechanical strength, dispersibility, light resistance, weather resistance, water repellency (resistance) and heat resistance and so on by addition of the graft chain of the polymer can be expected.

In addition, another example of chemical conversion of a polymer having an epoxy group is a crosslinking reaction by a diamine compound such as hexamethylenediamine, succinic anhydrate, 2-ethyl-4-methylimidazole, or the like, and an example of physicochemical conversion is a crosslinking reaction by irradiation with electron rays or the like. Among them, the reaction between PHA having an epoxy group on the side chain and hexamethylenediamine progresses in accordance with a scheme as described below to produce a crosslinked polymer.

[70]

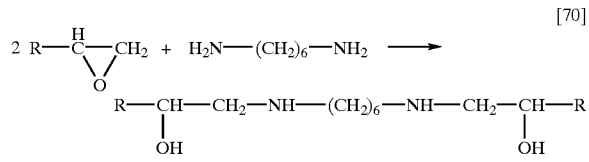

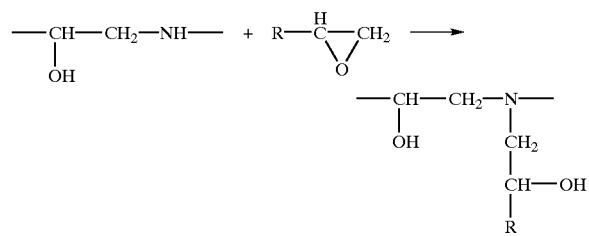

Because this micro-capsulated pigment has high pigment density and is very small, an image having satisfactory transparency and chromophoric properties, and being excellent in contrast can be formed by using a pigment ink containing this micro-capsulated pigment.

The step of processing the micro-capsulated pigment as a pigment ink is carried out by adding to an aqueous or oil medium the micro-capsulated pigment obtained in the previous step, further adding a dispersion stabilizer, preservative and the like as required for a various types of processes for production of pigment inks, and mixing together the same. This step can be distinguished between the case where the pigment ink is a water-based pigment ink and the case where the pigment ink is an oil-based pigment ink.

When the micro-capsulated pigment covered with PHA is used as a material for the water-based pigment ink, the micro-capsulated pigment can be used directly or as a water dispersed micro-capsulated pigment after removing the substrate in the following manner, depending the form provided for practical application. The reaction solution after an enzyme reaction is treated by a known method such as filtration under reduced pressure, filtration under pressure or centrifugation to obtain a water-bearing cake of pigment particles, and this cake is washed by water so that it is prevented from being dried to remove an unreacted substrate. Thereafter, the cake is dispersed in water by stirring with low shear or stirring with high shear by a homogenizer or the like, or using supersonic waves. For the purpose of supporting dispersion of the cake in water, a surfactant, a protective colloid and a water-soluble organic solvent may be added in amounts not causing significant reduction in resistance of the coating. Also, a preservative, a viscosity modifier, a pH modifier, a chelator and the like may be added.

Specifically, water-soluble organic solvents that may be added in the water-based pigment ink of the present invention include, for example, alcohols such as methyl alcohol, ethyl alcohol, n-butyl alcohol, isobutyl alcohol, tert-butyl alcohol, n-propyl alcohol and isopropyl alcohol; amides such as dimethyl formaldehyde and dimethyl acetamide; ketones such as acetone and methyl ethyl ketone; ethers such as tetrahydrofuran, dioxane, ethylene glycol methyl ether, ethylene glycol ethyl ether, diethylene glycol methyl ether, diethylene glycol ethyl ether, triethylene glycol monomethyl ether and triethylene ethylene glycol monoethyle ether; polyalcohols such as ethylene glycol, propylene glycol, butylene glycol, triethylene glycol, 1,2,6-hexanetriol, thiodiglycol, diethyleneglycol, polyethylene glycol, polypropylene glycol and glycerin; and N-methyl-pyrolidone and 1,3-dimethyl-2-imidazolidinone. For these compounds, one selected type may be used, or two or more types may be used in combination as required. The content of water-soluble organic solvent is preferably 95% by mass or lower, particularly preferably in the range of from 0 to 80% by mass.

Specifically, protective colloids that may be added in the water-based pigment ink of the present invention include natural proteins such as glue, gelatin, casein, albumin, acacia gum and fish glue, alginic acid, and synthetic polymers such as methylcellulose, carboxymethylcellulose, polyethylene oxide, hydroxyethylcellulose, polyvinyl alcohol, polyacryl amide, aromatic amide, polyacrylic acid, polyvinyl ether, polyvinyl pyrolidone, acryl and polyester. For these compounds, one selected type may be used, or two or more types may be used in combination as required. The protective colloid is used as required for the purpose of improving fixation, viscosity modification and drying properties, and the content of protective colloid in the ink is preferably 30% by mass or lower, particularly preferably 20% by mass or lower.

A surfactants that may be added in the water-based pigment ink of the present invention may be any of anionic, cationic, ampholytic and nonionic surfactants. Examples anionic surfactants include fatty esters such as sodium stearate, potassium oleate and semi-curable tallow fatty acid sodium; alkyl sulfates such as sodium dodecyl sulfate, tri(2-hydroxyethyl) ammonium dodecyl sulfate and sodium octadecyl sulfate; benzensulfonates such as sodium nonyl benzanesulfonate, sodium dodecyl benzenesulfonate, sodium otadecyl benzanesulfonate and sodium dodecyl diphenylether disulfonate; naphthalenesulfonates such as sodium dodecyl naphthalenesulfonate and naphthalene-sulfonic acid formalin condensates; sulfosuccinates such as sodium didodecyl sulfosuccinate and sodium dioctadodecyl sulfosuccinate; polyoxyethylene sulfates such as sodium polyoxyethylenedodecylether sulfate, tri(2-hydroxyethyl) ammonia polyoxyethylene dodecylether sulfate, sodium polyoxyethylene octadecylether sulfate and sodium polyoxyethylene dodecylphenylether sulfate; and phosphates such as potassium dodecyl phosphate and sodium octadecyl phosphate. Examples of cationic surfactants include alkyl amine salts such as octadecyl ammonium acetate and coconut oil amine acetate; and fourth ammonia salts such as dodecyl trimethyl ammonium chloride, octadecyl trimethyl ammonium chloride, dioctadecyl dimethyl ammonium chloride and dodecyl benzyl dimethyl ammonium chloride. Examples of ampholytic surfactants include alkyl betains such as dodecyl betain and octadodecyl betain; and amine oxides such as dodecyl dimethyl amine oxide. Examples of nonionic surfactants include polyoxyethylene alkyl ethers such as polyoxyethylene dodecyl ether, polyoxyethylene hexadecyl ether, polyoxyethylene octadecyl ether and polyoxyethylene (9-octadecenyl) ether; polyoxyethylene phenyl ethers such as polyoxyethylene octylphenyl ether and polyoxyethylene nonylphenyl ether; oxirane polymers such as polyethylene oxide and copolymer of ethylene oxide and propylene oxide; sorbitan fatty esters such as sorbitan dodecanoic ester, sorbitan hexadecanoic ester, sorbitan octadecanoic ester, sorbitan (9-octadecenoic) ester, sorbitan (9-octadecenoic) triester, polyoxyethylene sorbitan dodekanoic ester, polyoxyethylene sorbitan hexadecanoic ester, polyoxyethylene sorbitan octadecanoic ester, polyoxyethylene sorbitan octanoic triester, polyoxyethylene sorbitan (9-octadecenoic) ester and polyoxyethylene sorbitan (9-octadecenoic) triester; sorbitol fatty esters such as polyoxyethylene sorbitol (9-octadecenoic) tetraester; and glycerin fatty esters such as glycerin octadecanoic ester and glycerin (9-octadecenoic) ester. Of these surfactants, those with HLB larger than or equal to 14 are particularly preferable. The content of the above surfactant for use in the present invention is 0 to 10%, preferably 0 to 5% based on the total amount of water-based ink composition, although it varies depending on whether a single type of surfactant is used or two or more types of surfactants are used in combination.

For the process for production of the water-based pigment ink of the present invention, the ink can be produced only by stirring and mixing together a water-based dispersion containing a pigment covered with PHA, a water-soluble organic solvent, water, a protective colloid and the like by a simple stirrer such as a disper. In addition, as required, a surfactant, a preservative, a viscosity modifier, a pH modifier, a chelator and the like are added during stirring to produce the pigment ink. The water-based pigment ink composition of the present invention preferably contains 20 to 95% by mass of water and 1 to 60% by volume of pigment based on the total amount of the composition.

The water-based pigment ink produced in this way is used as pens such as a water-based ball point pen, a fountain pen, a water-based sign pen and a water-based maker, and a water-based recording liquid for on-demand type inkjet printers such as babble jet system, thermal jet system and piezo system ink jet printers, thereby making it possible to improve the fineness, chromophoric property, transparence, water resistance and redispersibility of the record image, and reduce costs for producing the recording liquid significantly by simplification of the dispersing step.

In the case where the micro-capsulated pigment covered with PHA is used as a material for oil-based pigment ink, the reaction solution after the enzyme reaction is treated by a known method such as filtration under reduced pressure, filtration under pressure or centrifugation to obtain a water-bearing cake of micro-capsulated pigment particles. This water-bearing cake is repeatedly washed with a non-aqueous medium to be used, after being dried or without being dried, thereby replacing the medium.

The non-aqueous medium in which the micro-capsulated pigment may be any pigment dispersion, particularly having low solvency for PHA and thus being capable of stably dispersing the micro-capsulated pigment, and may be selected from solvents that are used in normal pigment inks. It is desirable that one type or two or more types are selected for use from monovalent alcohols and polyvalent alcohols, and derivatives such as fatty ethers and carboxylates each having two carbon atoms with the vapor pressure at 20° C. in the range of from 0.0001 mmHg to 45 mmHg, in terms of safety associated with elimination of toxicity and offensive odors, drying characteristics of printed inks, and ease of handling.

Here, monovalent alcohols are preferably various kinds of well known alcohols each having two or more carbon atoms and one hydroxyl group in a molecule, for example ethanol, 1-propanol, 2-propanol, 1-butanol and 2-butanol, and monovalent alcohols each having a larger number of carbon atoms may also be used. Furthermore, derivatives thereof may be used. In addition, polyvalent alcohols include, for example, ethylene glycol, diethylene glycol, 3-methyl-1,3-butanediol, triethylene glycol, propylene glycol, dipropylene glycol, 1,3-propanediol, 1,3-butanediol, 1,5-pentanediol, hexylene glycol and octylene glycol each having two or more hydroxyl group in a molecule, and in addition thereto, organic solvents each having two or more hydroxyl groups in a molecule may be used without being limited as long as they do not cause product quality to be degraded. Glycol derivatives thereof may also be used.

In addition, ethers, esters and derivatives thereof include derivatives such as alkyl ethers (including aliphatic single ethers and aliphatic ethers) and carboxylates of the above described monovalent and polyvalent alcohols. First, alkyl ethers include, for example, methyl isopropyl ether, ethyl ether, ethyl propyl ether, ethyl butyl ether, isopropyl ether, butyl ether, ethylene glycol monomethyl ether, ethylene glycol monoethyl ether, ethylene glycol monobutyl ether, ethylene glycol dibutyl ether, diethylene glycol monomethyl ether, diethylene glycol monoethyl ether, diethylene glycol monobutyl ether, diethylene glycol diethyl ether, diethylene glycol dibutyl ether, propylene glycol monomethyl ether, dipropylene glycol monomethyl ether, tripropylene glycol monomethyl ether, tripropylene glycol monoethyl ether, propylene glycol monoethyl ether, propylene glycol butyl ether, dipropylene glycol n-butyl ether, tripropylene glycol n-butyl ether, propylene glycol phenyl ether, hexyl ether, 2-ethylene hexyl ether, ethylene glycol monohexyl ether, ethylene glycol monophenyl ether, ethylene glycol mono-2-ethyl butyl ether, propylene glycol ethyl ether, 3-methyl-3-methoxy-1-butanol, propylene glycol tertiary butyl ether, dipropylene glycol dimethyl ether. In addition thereto, ethers with 4 mole or more moles of ethylene oxide added to ethylene glycol, and ethers with 4 or more moles of propylene oxide added to propylene glycol are included.

Carboxylates include various esters, for example propylene glycol methyl ether acetate, propylene glycol diacetate, 3-methyl-3-methoxy butyl acetate, propylene glycol ethyl ether acetate, ethylene glycol ethyl ether acetate, butyl formate, isobutyl formate, isoamyl formate, propyl acetate, butyl acetate, isopropyl acetate, isobutyl acetate, isoamyl acetate, methyl propionate, ethyl propionate, propyl propyonate, isobutyl propyonate, isoamyl propionate, methyl butyrate, ethyl butyrate, propyl butyrate, methyl isobutyrate, ethyl isobutyrate, propyl isobutyrate, methyl valerate, ethyl valerate, propyl valerate, methyl isovalerate, ethyl isovalerate, propyl isovalerate, methyl trimethyl acetate, ethyl trimethyl acetate, propyl trimethyl acetate, methyl caproate, ethyl caproate, propyl caproate, methyl caprate, ethyl caprate, propyl caprate, methyl laurate, ethyl laurate, methyl oleate, ethyl aleate, capric triglyceride, citric tributyl acetate and octyl oxystearate.

These alcohols, and their derivatives including ethers and esters may be used alone, or in combination. Preferably, solvents other than ethylene glycol and the like are used in terms of safety, oral toxicity and the like. The content of the above described solvent for use in the present invention is 20 to 95% by mass, preferably 30 to 90% by mass based on the total amount of oil-based ink composition, although it varies depending on whether a single type of solvent is used or two or more types of solvents are used in combination.

In addition, for the oil-based pigment ink of the present invention, an anti-corrosive agent, mildewproofing agent, surfactant, lubricant, wetting agent and the like mutually soluble with the oil-based pigment ink may be added as required, and co-solvents may be added in terms of product performance as long as they do not impair stability of the ink. A nonvolatile solvent or the like may be added as a co-solvent for control of drying as long as the property of the product is not adversely affected. In addition, a dye may be used in combination as required for supporting a coloring agent as long as the ink is not badly affected.

Specifically, preservatives or mildewproofing agents include phenol, sodium ommazine, pentachlorophenol sodium, 1,2-benzisothiazolin 3-one, 2,3,5,6-tetrachloro-4-(methylsulfonil) pyridine, alkali metal salts of benzoic acid, sorbitanic acid and dehydroacetic acid such as sodium benzoate, and benzimidazole based compounds. Anti-corrosive agents specifically include benzotriazole, dicyclohexyl ammonium nitrite, diisopropyl ammonium nitrite and tolyl triazole. Lubricants and wetting agents specifically include polyether-modified silicones such as polyethylene glycol adducts of dimethyl polysiloxane.

The oil-based pigment ink composition preferably contains 20 to 95% by mass of the above described solbent and 1 to 50% by mass of pigment based on the total amount of composition.

The oil-based pigment ink produced in this way is used as pens such as an oil-based sign pen and an oil-based maker, and oil-based recording liquids such as a printing ink thereby making it possible to improve the fineness, chromophoric property, transparence, water resistance and redispersibility of the record image, and reduce costs for producing the recording liquid significantly by simplification of the dispersing step.

The present invention will be more specifically described below using Examples. However, each of the Examples that will be described below represents one example of the most preferred embodiments of the present invention, but the technical scope of the present invention should not be limited to these Examples.

REFERENCE EXAMPLE 1

Preparation of Transformant Capable of Producing PHA Synthesizing Enzyme, and Production of PHA Synthesizing Enzyme A transformant capable of producing the PHA synthesizing enzyme was prepared by the following method.

The YN2 strain was cultured on 100 ml of LB culture medium (1% polypeptone, 0.5% yeast extract, 0.5% sodium chloride, pH 7.4) at 30° C. overnight, followed by isolating and collecting chromosome DNA using a method by Marmer, et al. The obtained chromosome DNA was fully decomposed with a restriction enzyme Hind III. pUC18 was as a vector and cleaved by the restriction enzyme Hind III. Dephosphorylation of the terminal (Molecular Cloning, 1, 572, (1989); Cold Spring Harbor Laboratory Press.) was carried out, and thereafter DNA Ligation Kit Ver. 11 (Takara Shuzo Co., Ltd.) was used to couple the cleaved site (cloning site) of the vector to the Hind III fully decomposed fragment of the chromosome DNA. A plasmid vector with this chromosome DNA fragment incorporated therein was used to transform the *Escherichia coli* HB101 strain to prepare a DNA library of the YN2 strain.

Then, for selecting the DNA fragment including the PHA synthesizing enzyme gene of the YN2 strain, a probe for colony hybridization was prepared. Oligonucleotides composed of base sequences of SEQ ID NO: 5 and SEQ ID NO: 6 were synthesized (Amasham Pharmacia Biotech), and these oligonucleotides were used as primers to carry out PCR with the chromosome DNA as a template. The PCR-amplified DNA fragment was used as a probe. The labeling of the probe was carried out using the commercially available labeling enzyme AlkPhosDirect (Amasham Pharmacia-Biotech). The obtained labeled probe was used to select *Escherichia coli* strains having recombinant plasmids including PHA synthesizing enzyme genes from the chromosome DNA library of YN2 strains by the colony hybridization method. Plasmids were collected from the selected strains by the alkali method, whereby the DNA fragment including the PHA synthesizing enzyme gene can be obtained.

The gene DNA fragment obtained here was recombined into a vector pBBR 122 (Mo Bi Tec) including a broad-host-range replication region belonging to none of Inc P, Inc Q and Inc W constituting an incompatibility group. When this recombinant plasmid was transformed into the *Pseudomonas cichorii* YN2 ml strain (strain lacking PHA synthesis capability) by the Electroporation method, PHA synthesizing capability of the YN2 ml strain was recovered, thus exhibiting complement property. Thus, it is ensured that the selected gene DNA fragment includes a PHA synthesizing enzyme gene domain capable of being translated into the PHA synthesizing enzyme in *Pseudomonas cichorii* YN2 ml strain.

For this DNA fragment including the PHA synthesizing enzyme gene, base sequences were determined by the Sanger's method. As a result, it was found that in the determined base sequences, there existed base sequences expressed by SEQ ID NO: 2 and SEQ ID NO: 4, each coding a peptide. As described below, it could be ensured that the proteins composed of individual peptide chains all had enzyme activity, and the base sequences expressed by SEQ ID NO: 2 and SEQ ID NO: 4 were PHA synthesizing enzymes. Specifically, it was ensured that the base sequence of SEQ ID NO: 2 coded the amino acid sequence expressed by SEQ ID NO: 1, and the base sequence of SEQ ID NO: 4 coded the amino acid sequence expressed by SEQ ID NO: 3, and the PHA synthesis capability can be exhibited with a protein having only any one of these amino acid sequences.

For the PHA synthesizing enzyme gene of base sequence expressed by SEQ ID NO: 2, PCR was carried out with Chromosome DNA as a template to reprepare the full length of the PHA synthesizing enzyme.

For the base sequence expressed by SEQ ID NO: 2, oligonucleotide having base sequences upstream to its initiation codon (SEQ ID NO: 7), which serves as an upstream primer, and oligonucleotide having base sequences downstream to its stop codon (SEQ ID NO: 8), which serves as a downstream primer were designed and synthesized, respectively (Amasham Pharmacia·Biotech) Using these oligonucleotides as primers, PCR was carried out with chromosome DNA as a template to amplify the full length of the PHA synthesizing enzyme gene (LA-PCR Kit; Takara Shuzo Co., Ltd.)

In a similar way, for the PHA synthesizing enzyme gene of base sequence expressed by SEQ ID NO: 4, PCR was carried out with Chromosome DNA as a template to reprepare the full length enzyme of the PHA synthesizing enzyme. For the base sequence expressed by SEQ ID NO: 4, oligonucleotide having base sequences upstream to its initiation codon (SEQ ID NO: 9), which serves as an upstream primer, and oligonucleotide having base sequences downstream to its stop codon (SEQ ID NO: 10), which serves as a downstream primer were designed and synthesized, respectively (Amasham Pharmacia-Biotech). Using this oligonucleotide as a primer, PCR was carried out to amplify the full length gene of the PHA synthesizing enzyme (LA-PCR Kit; Takara Shuzo Co., Ltd.)

Then, PCR amplified fragment including the obtained full length gene of PHA synthesizing enzyme were each fully decomposed using the restriction enzyme Hind III. In addition, the expression vector pTrc99A was also cleaved with the restriction enzyme Hind III, and was subjected to dephosphorylation processing (Molecular Cloning, vol. 1, p. 572, 1989; Cold Spring Harbor Laboratory Press). A DNA fragment including the full length gene of the PHA synthesizing enzyme gene with unnecessary base sequences at both terminals removed was coupled to the cleaved site of this expression vector pTrc99A using DNA Ligation Kit Ver. II (Takara Shuzo Co., Ltd.).

*Escherichia coli* (HB101: Takara Shuzo Co., Ltd.) was transformed by a potassium chloride method using the obtained recombinant plasmid. The obtained recombinant was cultured, amplification of recombinant plasmid was carried out, and the recombinant plasmid was collected for each type. The recombinant plasmid retaining gene DNA of SEQ ID NO: 2 was defined as pYN2-C1 (derived from SEQ ID NO: 2), and the recombinant plasmid retaining gene DNA of SEQ ID NO: 4 was defined as pYN2-C2 (derived from SEQ ID NO: 4).

*Escherichia coli* (strain HB101fB, fadB deficient mutant) was transformed by a potassium chloride method using pYN2-C1 and pYN2-C2 to obtain recombinant *Escherichia coil* strains, a pYN2-C1 recombinant strain and a pYN2-C2 recombinant strain each having its own recombinant plasmid.

The pYN2-C1 recombinant strain and pYN2-C2 recombinant strain were each plated in 200 ml of M9 medium containing 0.5% of yeast extract and 0.1% of octanoic acid, and were subjected to shaking culture at 37° C. and 125 strokes/minute. After 24 hours, cells were collected by centrifugation, and plasmid DNA was collected using an ordinary method.

For pYN2-C1, oligonucleotide serving as an upstream primer (SEQ ID NO: 11) and oligonucleotide serving as a downstream primer (SEQ ID NO: 12) were each designed and synthesized (Amasham Pharmacia-Biotech). Using these oligonucleotides as primers, PCR was carried out with pYN2-C1 as a template to amplify the full length gene of the PHA synthesizing enzyme having the BamHI restriction site in the upstream and the XhoI restriction site in the downstream (LA-PCR Kit; Takara Shuzo Co., Ltd.).

In a similar way, for pYN2-C2, oligonucleotide serving as an upstream primer (SEQ ID NO: 13) and oligonucleotide serving as a downstream primer (SEQ ID NO: 14) were each designed and synthesized (Amasham Pharmacia·Biotech). Using this oligonucleotide as a primer, PCR was carried out with pYN2-C2 as a template to amplify the full length gene of the PHA synthesizing enzyme having the BamHI restriction site in the upstream and the XhoI restriction site in the downstream (LA-PCR Kit; Takara Shuzo Co., Ltd.).

Each of purified PCR amplified products was digested by BamHI and XhoI, and was inserted into a corresponding site of plasmid pGEX-6P-1 (manufactured by Amasham Pharmacia·Biotech Co., Ltd.). These vectors were used to transform *Escherichia coli* (JM109) to obtain a strain for expression. The strain was checked with DNA fragments obtained by treating with BamHI and XhoI plasmid DNA prepared in large quantity using Miniprep (Wizard Minipreps DNA Purification Systems, manufactured by PROMEGA Co., Ltd.). The obtained strain was pre-cultured in 10 mL of LB-Amp medium overnight, and thereafter 0.1 mL of the strain was added in 10 mL of LB-Amp medium, and was shaking-cultured at 170 rpm at 37° C. for 3 hours. Thereafter, IPTG was added (at a final concentration of 1 mM), and culture was continuously carried out at 37° C. for 4 to 12 hours.

IPTG-induced *Escherichia coli* was collected (8000×g, 2 minutes, 4° C.), and was resuspended in 1 ml of PBS at 4° C. The cells were crushed by freezing and thawing and sonication, and were subjected to centrifugation (8000×g, 10 minutes, 4° C.) to remove solid contaminants. The presence of desired expression proteins in the supernatant was confirmed with SDS-PAGE, followed by purifying the induced and expressed GST fused protein with Glutathion Sepharose 4B beads (manufactured by Amasham Pharmacia·Biotech Co., Ltd.).

The glutathion sepharose for use in the purification was treated for curbing nonspecific adsorption in advance. Specifically, the glutathion sepharose was washed three times with the same amount of PBS (8000×g, 1 minute, 4° C.), and thereafter the same amount of PBS containing 4% BSA was added to treat the glutathion sepharose at 4° C. for 1 hour. After treatment, the glutathion sepharose was washed two times with the same amount of PBS, and was resuspended in ½ in quantity of PBS. 40 μL of pretreated glutathion sepharose was added to 1 mL of cell-free extract and stirred gently at 4° C. Thereby, the fused proteins GST-YN2-C1 and GST-YN2-C2 were adsorbed to glutathion sepharose.

After they were adsorbed, glutathion sepharose was collected by centrifugation (8000×g, 1 minute, 4° C.), and was washed three times with 400 μL of PBS. Thereafter, 40 μL of 10 mM of glutathion was added, and was stirred at 4° C. for 1 hour to elute the adsorbed fused protein. The supernatant was collected after centrifugation (8000×g, 2 minutes, 4° C.), and thereafter dialysis was conducted against PBS to purify the GST fused protein. It was confirmed by SDS-PAGE that the protein exhibited a single band.

500 μg of each GST fused protein was digested by PreScission protease (Amasham Pharmacia-Biotech, 5 U), and was thereafter passed through glutathion sepharose to remove the protease and GST. Flow-through fractions were further processed with a sephadex G200 column equilibrated with PBS to obtain final purified expression proteins YN2-C1 and Yn2-C2. It was confirmed by SDS-PAGE that they exhibited single bands of 60.8 kDa and 61.5 kDa, respectively.

Each crude enzyme solution was concentrated using a biological solution sample concentrating agent (Mizubutorikun AB-1100, manufactured by Ato Co., Ltd.) to obtain 10 U/ml of purified enzyme solution.

The activity of each purified enzyme was measured by the aforesaid method. Also, the concentrations of proteins in the sample were measured by the Micro BCA protein quantification reagent kit (Pierce Chemical Co., Ltd.). The result of measuring the activity of each purified enzyme is shown in Table 1.

TABLE 1

|  | Activity | Specific Activity |
|---|---|---|
| YN2-C1 | 2.1 U/mL | 4.1 U/mg Protein |
| YN2-C2 | 1.5 U/mL | 3.6 U/mg Protein |

REFERENCE EXAMPLE 2

Production of PHA Synthesizing Enzyme 2

P91, H45, YN2 or P161 strain was plated in the 200 ml of M9 medium containing 0.5% of yeast extract (manufactured by Difco Co., Ltd.) and 0.1% of octanoic acid, and was subjected to shaking culture at 30° C. and 125 strokes/minute. After 24 hours, cells were collected by centrifugation (10,000×g, 4° C., 10 minutes), and were resuspended in 200 ml of 0.1 M Tris HCl buffer (pH 8.0) and subjected to centrifugation again, thereby washing the cells. The cells were resuspended in 2.0 ml of 0.1 M Tris HCl buffer (pH 8.0) and crushed by a supersonic crusher, followed by centrifugation (12,000×g, 4° C., 10 minutes) and collection of a supernatant to obtain a crude enzyme. The result of measuring activity of each crude enzyme is shown in Table 2.

TABLE 2

|  | Activity |
|---|---|
| P91 strain | 0.1 U/mL |
| H45 strain | 0.2 U/mL |
| YN2 strain | 0.4 U/mL |
| P161 strain | 0.2 U/mL |

Each crude enzyme solution was concentrated using a biological solution sample concentrating agent (Mizubutorikun AB-1100, manufactured by Ato Co., Ltd,) to obtain 10 U/ml of purified enzyme solution.

REFERENCE EXAMPLE 3

Synthesis of 3-hydroxyacyl CoA (R)-3-hydroxyoctanoyl-CoA was synthesized in accordance with the following procedure, based on the method of Rehm BHA, Kruger N, Steinbuchel A (1998) Journal of Biological Chemistry 273 pp 24044–24051, with the method slightly modified. Acyl-CoA synthetase (manufactured by Sigma Co., Ltd.) was dissolved in a tris hydrochloric buffer solution (50 mM, pH 7.5) containing 2 mM ATP, 5 mM MgCl$_2$, 2 mM CoA and 2 mM (R)-3-hydroxyoctanoate so that the concentration was 0.1 milliunit per microliter. The solution was stored in a hot bat at 37° C., and was sampled at appropriate times to analyze the progress of the reaction by HPLC. Sulfuric acid was added in the sampled reaction solution to make a concentration 0.02 N to stop the enzyme reaction, and thereafter (R)-3-hydroxyoctanoate being an unreacted substrate was extracted with n-heptane and removed. For the analysis by HPLC, using a RP18 column (nucleosil C18, 7 μm, Knauser), elution was conducted with the linear concentration gradient of acetonitrile using a 25 mM phosphate buffer solution (pH 5.3) as a mobile phase, and absorption spectra of 200 to 500 nm were monitored by a diode array detector, thereby detecting a thioester compound produced through the enzyme reaction. In a similar way, (R)-3-hydroxy-5-phenylvaleryl CoA, (R)-3-hydroxy-5-(4-fluorophenyl) valeryl CoA, (R,S)-3-hydroxy-5-phenoxyvaleryl CoA and (R,S)-3-hydroxy-7,8-epoxyoctanoyl CoA were prepared. Furthermore, (R,S)-3-hydroxy-7,8-epoxyoctanoic acid for use in preparation of (R,S)-3-hydroxy-7,8-epoxyoctanoyl CoA was prepared by epoxidizing unsaturated parts of 3-hydroxy-7-octenoic acid synthesized by the method described in Int. J. Biol. Macromol., 12, 85–91 (1990) with 3-chlorobenzoic acid.

EXAMPLE 1

Preparation of Micro-Capsulated Pigment 1

Carbon black was suspended in the concentration of 25% by mass as a pigment in a 20 mM phosphate buffer solution (pH 7.0) with 1% by mass of Tween-20 added therein as a surfactant. They were mixed by a ball mill to prepare a dispersion of carbon black. According to the laser light scattering method, the carbon black was monodispersed with the average particle size of 102 nm.

The PHA synthesizing enzyme YN2-C1 derived from *Pseudomonas cichorii* YN2 prepared in Reference Example 1 was added to make a concentration 100 U/mL, and was left to stand at 20° C. for 30 minutes. Then, (R)-3-hydroxyoctanoyl CoA prepared in Reference Example 3 was added at a final concentration of 5 mM. A synthesis reaction was carried out by incubating the resulting solution at 37° C. for 30 minutes.

The reaction solution was subjected to centrifugation (10,000×g, 4° C., 10 minutes) to obtain a water-bearing cake of micro-capsulated pigment with carbon black as a core. This water-bearing cake was resuspended in ethanol, followed by collecting micro-capsulated pigment again by centrifugation operation. This operation was repeated three times to carry out cleaning.

Figure 1B:
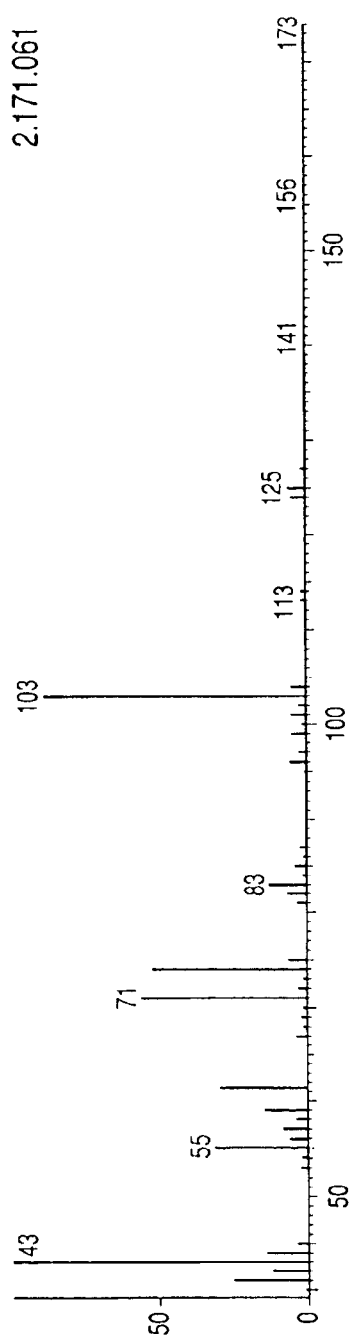

A portion of the obtained water-bearing cake of micro-capsulated pigment was dried under reduced pressure and thereafter suspended in 20 ml of chloroform and stirred at 60° C. for 20 hours to extract PHA constituting shells. The extract was filtered by a membrane filter having a pore size of 0.45 μm, and was concentrated under reduced pressure by a rotary evaporator, followed by carrying out methanolysis in accordance with an ordinary method and conducting analyses by a gas chromatography-mass spectrometer (GC-MS, Shimadzu QP-5050, EI method) to identify methyl-esterified PHA monomer units. As a result, the PHA was found to be PHA having 3-hydroxyoctanoic acid as a monomer unit as shown in FIGS. 1A and 1B. In addition, the molecular weight of the PHA was examined by gel permeation chromatography (GPC; Toso HLC-8020, column; Polymer laboratory PL gel MIXED-C (5 μm), solvent; chloroform, column temperature; 40° C., polystyrene equivalent) to obtain the result of Mn=16,000 and Mw=36,000.

According to the laser light scattering method, the micro-capsulated pigment were monodispersed with the average particle size of 140 nm.

EXAMPLE 2

Preparation of Micro-Capsulated Pigment 2

A phthalocyanine based organic pigment, Pigment Blue 60 was suspended in the concentration of 25% by mass as a pigment in a 20 mM phosphate buffer solution (pH 7.0) with 1% by mass of Tween-20 added therein as a surfactant. They were mixed by a ball mill to prepare a dispersion of Pigment Blue 60. According to the laser light scattering method, the Pigment Blue 60 was monodispersed with the average particle size of 105 nm.

The PHA synthesizing enzyme YN2-C2 derived from *Pseudomonas cichorii* YN2 prepared in Reference Example 1 was added to make a concentration was 100 U/mL, and was left to stand at 20° C. for 30 minutes. Then, (R)-3-hydroxy-5-phenylvaleryl CoA prepared in Reference Example 3 was added at a final concentration of 5 mM. A synthesis reaction was carried out by incubating the resulting solution at 37° C. for 30 minutes.

The reaction solution was subjected to centrifugation (10,000×g, 4° C., 10 minutes) to obtain a water-bearing cake of micro-capsulated pigment with Pigment Blue 60 as a core. This water-bearing cake was resuspended in water, followed by collecting the micro-capsulated pigment again by centrifugation operation. This operation was repeated three times to carry out cleaning.

Figure 2A:
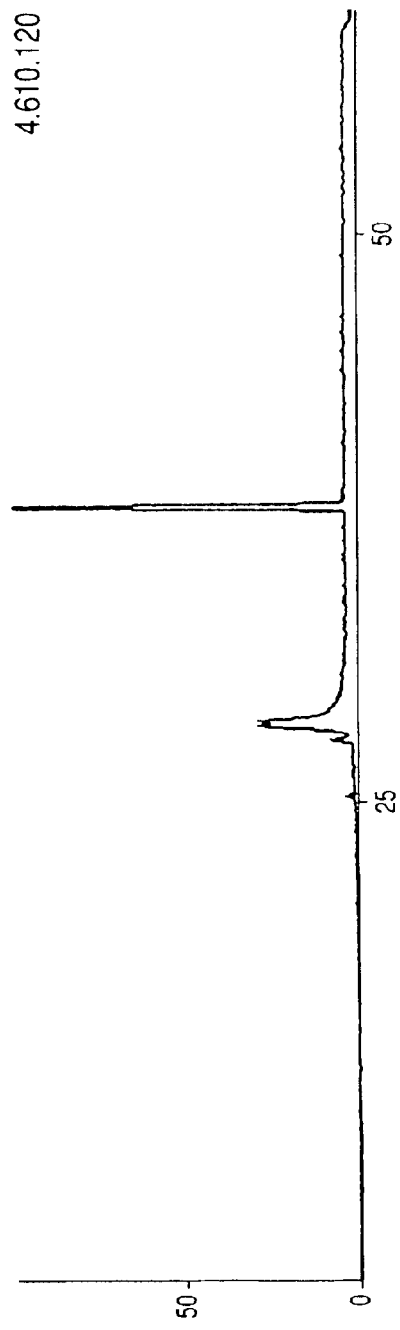
FIGS. 2A and 2B show the results of GC-MS analyses of shells of pigment dispersions of Example 2.
Figure 2B:
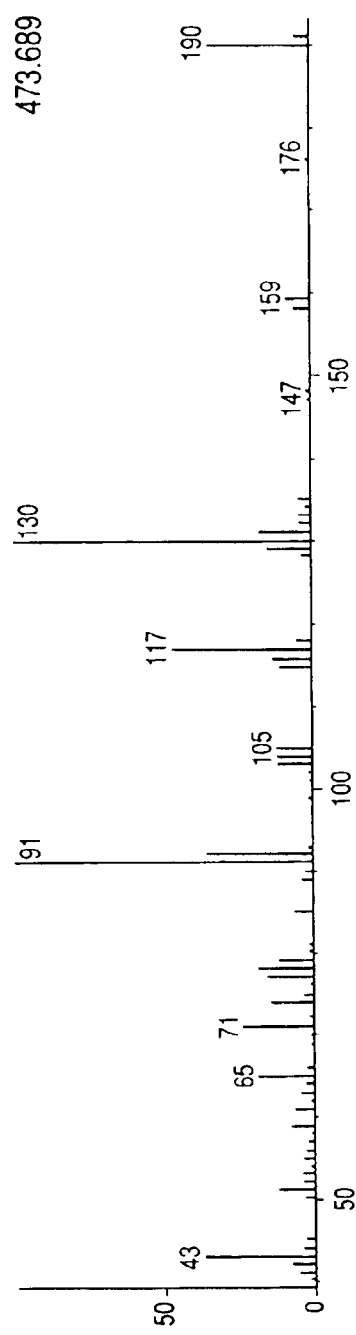

A portion of the obtained water-bearing cake of micro-capsulated pigment was dried under reduced pressure and thereafter suspended in 20 ml of chloroform and stirred at 60° C. for 20 hours to extract PHA constituting shells. The extract was filtered through a membrane filter having a pore size of 0.45 µm, and was concentrated under reduced pressure by a rotary evaporator, followed by carrying out methanolysis in accordance with an ordinary method and conducting analyses by a gas chromatography-mass spectrometer (GC-MS, Shimadzu QP-5050, EI method) to identify methyl-esterified PHA monomer units. As a result, the PHA was found to be PHA having 3-hydroxy-5-phenylvaleric acid as a monomer unit as shown in FIGS. 2A and 2B. In addition, the molecular weight of the PHA was examined by gel permeation chromatography to obtain the result of Mn=16,000 and Mw=36,000.

According to the laser light scattering method, the micro-capsulated pigment were monodispersed with the average particle size of 145 nm.

EXAMPLE 3

Preparation of Micro-Capsulated Pigment 3

As a pigment serving as a core, an azo based pigment, Pigment Yellow 12 and a condensation polycyclic pigment, Pigment Red 170 were suspended and dispersed in water in a same manner as Example 2. The PHA synthesizing enzyme derived from H45 and P161 strains prepared in Reference Example 2 was added to each pigment dispersion so that the concentration was 100 U/mL, and was left to stand at 20° C. for 30 minutes. Then, (R)-3-hydroxy-5-(4-fluorophenyl) valeryl CoA prepared in Reference 3 was added at a final concentration of 5 mM. A synthesis reaction was carried out by incubating the resulting solution at 37° C. for 30 minutes. Pigment covered with PHA were collected in the same manner as Example 2.

Figure 3A:
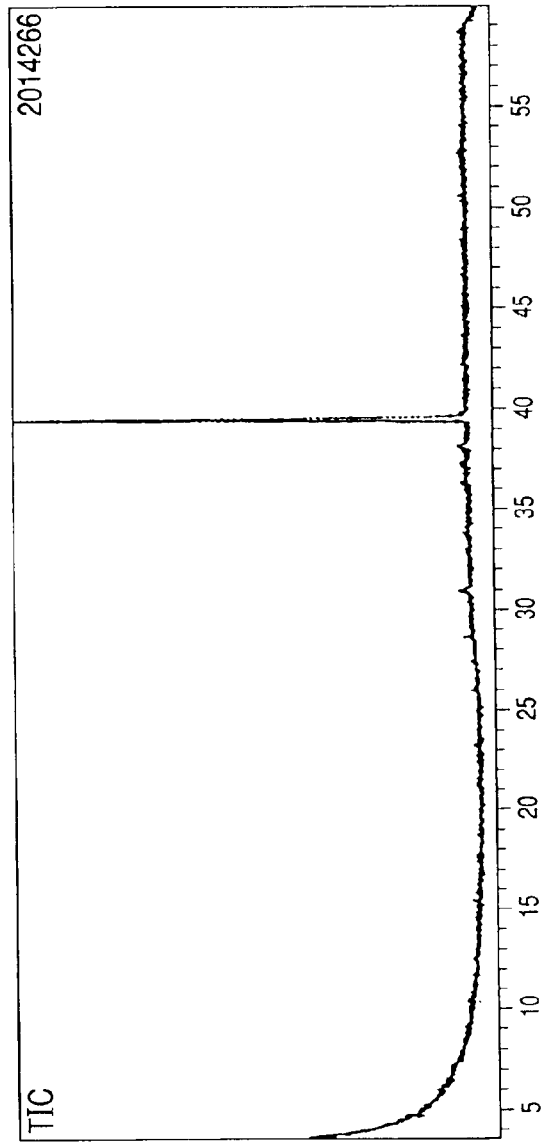
FIGS. 3A and 3B show the results of GC-MS analyses of shells of pigment dispersions of Example 3.
Figure 3B:
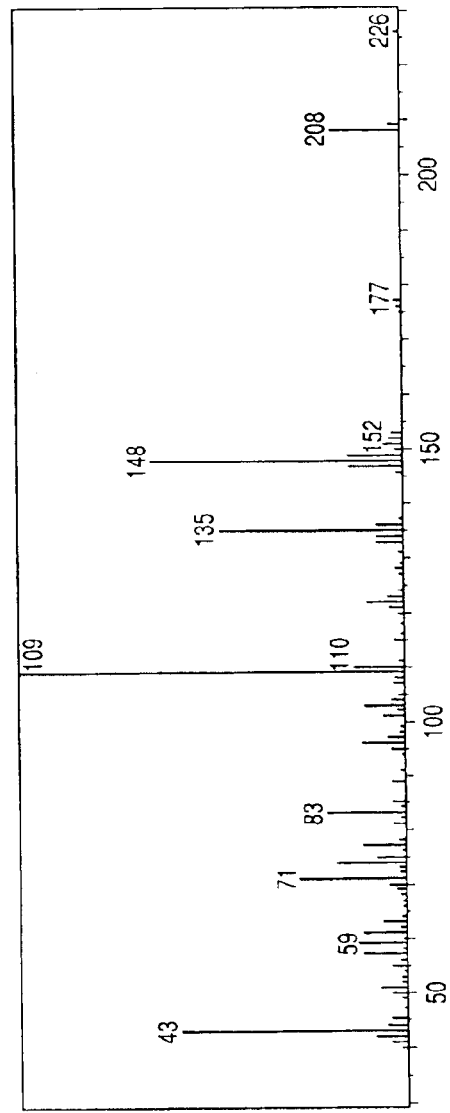

PHA constituting the shell of the micro-capsulated pigment was extracted to identify the methyl-esterified PHA monomer unit in a same manner as Example 2. As a result, the PHA was found to be PHA having (R)-3-hydroxy-5-(4-fluorophenyl) valeric acid as a monomer unit as shown in FIGS. 3A and 3B. In addition, the molecular weight of the PHA was examined by gel permeation chromatography to obtain the result of Mn=16,000, Mw=36,000 and Mn=15,000 and Mw=35,000.

According to the laser light scattering method, the micro-capsulated pigment were monodispersed with the average particle sizes of 160 nm and 170 nm, respectively.

EXAMPLE 4

Preparation and Evaluation of Water-Based Pigment Ink

The black micro-capsulated pigment prepared in Example 1 was used to prepare a water-based black ink. The composition of the black ink is as follows. Furthermore, the amount of each component shown below refers to parts by mass. A dispersing stirrer (TK Homodisper 20 manufactured by Tokushu Kika Kogyo Co., Ltd.) was used to carry out dispersion for 3 hours.
Black micro-capsulated pigment: 50 parts;
Glycerin: 6 parts;
Diethylene glycol: 7 parts;
Polyoxyethylene dodecyl ether: 0.2 parts;
Proxel XL-2: Preservative (manufactured by ZENECA Co., Ltd.): 0.3 parts;
Benzotriazole: corrosion inhibitor (manufactured by Kanto Kagaku Co., Ltd.): 0.005 parts; and
Water: remainder.

In a similar way, the blue micro-capsulated pigment prepared in Example 2 was used to prepare a water-based blue ink. The composition of the blue ink is as follows.
Blue micro-capsulated pigment: 50 parts;
Glycerin: 6 parts;
Diethylene glycol: 7 parts;
Polyoxyethylene dodecyl ether: 0.2 parts;
Proxel XL-2: Preservative (manufactured by ZENECA Co., Ltd.): 0.3 parts;
Benzotriazole: corrosion inhibitor (manufactured by Kanto Kagaku Co., Ltd.): 0.005 parts; and
Water: remainder.

In a similar way, the yellow and red micro-capsulated pigments prepared in Example 3 were used to prepare a water-based yellow ink and a water-based red ink. The compositions of the inks are as follows.
(Yellow Ink)
Yellow micro-capsulated pigment: 50 parts;
Glycerin: 6 parts;
Diethylene glycol: 7 parts;
Polyoxyethylene dodecyl ether: 0.2 parts;
Proxel XL-2: Preservative (manufactured by ZENECA Co., Ltd.): 0.3 parts;
Benzotriazole: corrosion inhibitor (manufactured by Kanto Kagaku Co., Ltd.): 0.005 parts; and
Water: remainder.
(Red Ink)
Red micro-capsulated pigment: 50 parts;
Glycerin: 6 parts;
Diethylene glycol: 7 parts;
Polyoxyethylene dodecyl ether: 0.2 parts;
Proxel XL-2: Preservative (manufactured by ZENECA Co., Ltd.): 0.3 parts;
Benzotriazole: corrosion inhibitor (manufactured by Kanto Kagaku Co., Ltd.): 0.005 parts; and
Water: remainder.

As a comparative example of a water-based pigment dispersion not covered with polyhydroxyalkanoate, finely crushed carbon black was used to prepare a water-based pigment ink of Comparative Example having the following composition.
Finely crushed carbon black: 50 parts;
Glycerin: 6 parts;

Diethylene glycol: 7 parts;
Polyoxyethylene dodecyl ether: 0.2 parts;
Proxel XL-2: Preservative (manufactured by ZENECA Co., Ltd.): 0.3 parts;
Benzotriazole: corrosion inhibitor (manufactured by Kanto Kagaku Co., Ltd.): 0.005 parts; and
Water: remainder.

The dispersion stability and average particle size were evaluated for the water-based inks prepared in this way. For the dispersion stability, the ratio in height of a translucent portion of the upper layer resulting from sedimentation of pigment to the total dispersion was measured using as a measure a level of phase separation after storage at 70° C. for 3 days. For the average particle size, a median diameter measured by a Laser Doppler type grain size analyzer Micro Track (UPA 150 manufactured by Lease & North Lope Co., Ltd.) was defined as an average particle size.

TABLE 3

|  | Phase separation [%] | Average particle size [nm] | |
|---|---|---|---|
|  |  | Immediately after regulation | 70° C. After 3 days |
| Black Ink | 0 | 173 | 184 |
| Blue Ink | 0 | 154 | 165 |
| Yellow Ink | 0 | 182 | 183 |
| Red Ink | 0 | 166 | 178 |
| Comparative Example | 25 | 289 | 1865 |

As apparent from Table 3, the ink prepared with pigment particles covered with polyhydroxyalkanoate according to the present invention has excellent dispersion stability irrespective of the structure of pigments, from the fact that the particle size of the pigment microcapsule was not significantly changed even after the ink was produced as a water-based recording liquid, and no phase separation occurred. This is particularly a useful effect in uses of inks for ink jet printers such that ink is discharged from very small nozzles for trajectory recording.

EXAMPLE 5

Evaluation as Ink for Ink Jet Printer

Using the ink of the above Example 4, an ink jet printer comprising a recording head with resolution of 360 dpi was used to carry out printing at intervals of 720 dpi in the main scanning direction at a discharge frequency of 7.2 kHz. A drop of ink was shot onto a pixel formed in resolution of 360 dpi to 720 dpi to conduct recording with the amount of discharge per drop of ink from the recording head being about 25 picoliters. Then, solid images and character patterns were printed to evaluate the OD, dot periphery shape, solid uniformity, strike-through property, smoothing property and circularity of images. PB paper manufactured by Canon Inc. was used as a print medium.

For the OD, the portion of solid pattern of a 5 mm square was measured.

For the dot periphery shape, sharpness of the edge portion of a line image was visually observed by a magnifier.
A: The edge of line is neatly drawn in line form.
B: The linearity of the edge of line is slightly lost, but it does not pose any problem for practical use.
D: The linearity of the edge of line is lost.
For the solid uniformity, uniformity of density in a solid pattern of a 5 mm square was visually observed.
A: White decolored portions are not found.
B: White decolored portions are found, but are not so prominent that they do not pose a problem for practical use.
D: White decolored portions are so prominent that the image quality is adversely affected.

For the strike-through property, the portion in which a solid pattern had been printed was visually observed from the back side to check whether or not the pattern could be seen through the medium, and optical density of the corresponding portion of the back face was measured using a Macbeth densitometer.
A: Almost no pattern is seen, and the optical density measured by the Macbeth densitometer is smaller than 0.2. B: The pattern is slightly seen, but is almost negligible, and the optical density measured by the Macbeth densitometer is in the range of from 0.2 to 0.25.

For the circularity, the shapes of ink dots formed on the print medium by a drop of ink were observed by a magnifier.
A: Almost all dots are close to circles from a statistical viewpoint.
B: From a statistical viewpoint, circularity is lost for some dots, but there is no problem for formation of images. C: From a statistical viewpoint, circularity is lost for a great number of dots, and distorted dots are formed.

The results of the above evaluation are shown in Table 4.

TABLE 4

|  | Black Ink | Blue Ink | Yellow Ink | Red Ink | Comparative Example |
|---|---|---|---|---|---|
| OD | 1.45 | 1.47 | 1.45 | 1.46 | 1.10 |
| Dot diameter (μm) | 67 | 70 | 72 | 69 | 48 |
| Dot periphery shape | A | A | A | A | D |
| Solid uniformity | A | A | A | A | D |
| Strike-through property | A | A | A | A | B |
| Circularity | A | A | A | A | C |

As apparent from Table 4, when the ink prepared from pigment particles covered with polyhydroxyalkanoate according to the present invention is used, a coagulated pigment on the recording medium (paper) is dispersed uniformly in ink dots in the form of fine particles, thereby making it possible to obtain ink dots excellent in peripheral and outer shapes, having appropriately widened dot diameters, having uniform distribution of image density in dots, and being almost free from feathering.

EXAMPLE 6

Preparation and Evaluation of Oil-Based Pigment Ink

The black micro-capsulated pigment prepared in Example 1 was used to prepare an oil-based black ink. The composition of the black ink is as follows. Furthermore, the amount of each component shown below refers to parts by mass. A dispersing stirrer (TK Homodisper 20 manufactured by Tokushu Kika Kogyo Co., Ltd.) was used to carry out dispersion for 3 hours. For a solvent, propylene glycol monomethyl ether acetate was used.
Black micro-capsulated pigment: 30 parts;
Glycerin: 6 parts;
Diethylene glycol: 7 parts;
Polyoxyethylene dodecyl ether: 0.2 parts; and
Solvent: remainder.

An oil-based black ink having the following composition was prepared as a control.
Black micro-capsulated pigment: 30 parts;
Glycerin: 6 parts;
Diethylene glycol: 7 parts;

Polyoxyethylene dodecyl ether: 0.2 parts;
Rosin phenol resin: 25 parts; and
Solvent: remainder When both the black inks were compared, no difference was found for the size of pigment particles in the ink and dispersion stability, but the viscosity of the former was lower than that of the latter. That is, it has been found that the pigment ink of the present invention has good dispersion stability even though a synthetic resin such as rosin phenol resin or ketone resin that is usually added in an oil-based pigment ink as a dispersion stabilizing resin is not added. This is particularly a useful effect in use of pens such as an oil-based sign pen and an oil-based marker, and oil-based recording liquids such as a printing ink, because the pigment density is relatively increased and the color rendering property is improved.

EXAMPLE 7

Preparation of Water-Based Pigment Ink

A dispersion solution of carbon black was prepared as a pigment in a same manner as Example 1, and PHA synthesizing enzyme YN2-C1 originating from *Pseudomonas cichorii* YN2 was added therein so that the concentration was 100 U/mL, and was left to stand at 20° C. for 30 minutes.

Then, (R)-3-hydroxyoctanoyl CoA prepared in Reference Example 3 was added so that the final concentration was 5 mM, and was incubated at 37° C. for 25 minutes. In addition, (R)-3-hydroxypimelyl CoA (prepared by the method described in Eur. J. Biochem., 250, 432–439 (1997)) was added so that the final concentration was 1 mM, and was incubated at 37° C. for 5 minutes.

The reaction solution was subjected to centrifugation (10,000×g, 4° C., 10 minutes) to obtain a water-bearing cake of micro-capsulate pigment with carbon black as a core. This water-bearing cake was resuspended in water, followed by collecting the micro-capsulated pigment by centrifugation again. This operation was carried out three times to conduct washing.

Then, the weight of the polymer formed on the surfaces of the obtained micro-capsulated pigment was measured by a time-of-flight secondary ion mass spectrometer (TOF-SIMS IV, manufactured by CAMECA Co., Ltd.). From the obtained mass spectrum, it was found that the surface of the micro-capsulated pigment was constituted by a copolymer of polyhydroxypimelate and polyhydroxyoctanoate in the molar ratio of 1.6:1. In addition, the mass spectrum was measured by TOF-SIMS in a similar way while cutting gradually the surface of the micro-capsulated pigment by ion sputtering, and it was found that the polymer constituting the micro-capsulated pigment changed to a homopolymer of polyhydroxyoctanoate. From this fact, it has been found that the micro-capsulated pigment of this Example is a micro-capsulated pigment in which polyhydroxyoctanoate with which the pigment is covered is further covered with ionic and water-dispersible polyhydroxypimelate.

In addition, the molecular weight of the PHA was examined by gel permeation chromatography (GPC; Toso HLC-8020, column; Polymer laboratory PL gel MIXED-C (5 μm), solvent; chloroform, column temperature; 40° C., polystyrene equivalent) to obtain the result of Mn=19,000 and Mw=39,000.

According to the laser light scattering method, the micro-capsulated pigment was monodispersed with the average particle size of 151 nm.

This black micro-capsulated pigment was used to prepare a water-based black ink without using a surfactant. The composition of the black ink is as follows, and is similar to that of Example 4 except that polyoxyethylene dodecyl ether in not used. Furthermore, the amount of each component shown below refers to parts by mass. A dispersing stirrer (TK Homodisper 20 manufactured by Tokushu Kika Kogyo Co., Ltd.) was used to carry out dispersion for 3 hours.

Black micro-capsulated pigment: 50 parts;
Glycerin: 6 parts;
Diethylene glycol: 7 parts;
Proxel XL-2: Preservative (manufactured by ZENECA Co., Ltd.): 0.3 parts;
Benzotriazole: corrosion inhibitor (manufactured by Kanto Kagaku Co., Ltd.): 0.005 parts; and
Water: remainder.

For the water-based ink prepared in this way, dispersion stability was evaluated in a same manner as Example 4. As a result, phase separation of the water-based ink of this Example was 0% as in the case of the water-based ink of Example 4 using a surfactant. Thereby, it has been found that a water-based ink having excellent dispersion stability can be provided without using a surfactant by preparing a micro-capsulated pigment with hydrophilic PHA.

EXAMPLE 8

Preparation of Oil-Based Pigment Ink Using Inorganic Pigment 1

Red oxide as an inorganic red pigment was dispersed by a sand mill so that the size was 0.3 μm or smaller, and the particle size was uniformed by a settling process. When the average particle size of this pigment was measured by a laser light scattering method, it was monodispersed with the size of 152 nm. 10 parts by mass of crude enzyme of PHA synthesizing enzyme (10 U/ml) originating from P161 and 39 parts by weigh of PBS were added to one part by mass of this pigment, and were gently shaken at 30° C. for 30 minutes to adsorb the PHA synthesizing enzyme to the surface of the pigment. This was subjected to centrifugation (10,000×g, 4° C., 10 minutes), the precipitate was suspended in the PBS solution, and centrifugation (10,000×g, 4° C., 10 minutes) was carried out again to obtain a fixed enzyme.

The above fixed enzyme was suspended in 48 parts by mass of 0.1 M phosphate buffer (pH 7.0), and one part by mass of (R)-3-hydroxyoctanoyl CoA (prepared by Eur. J. Biochem., 250, 432–439 (1997)) and 0.1 parts by mass of bovine serum albumin (manufactured by Sigma Co., Ltd.) were added therein, and were gently shaken at 37° C. for 30 minutes.

After the reaction, the reaction solution was subjected to centrifugation (10,000×g, 4° C., 10 minutes), and precipitated particles were dried under reduced pressure to obtain a micro-capsulated pigment.

Then, the weight of the polymer formed on the surfaces of this micro-capsulated pigment was measured by a time-of-flight secondary ion mass spectrometer (TOF-SIMS IV, manufactured by CAMECA Co., Ltd.). From the obtained mass spectrum, it was found that the surface of the capsule structure was constituted by a homopolymer of polyhydroxyoctanoate. In addition, the mass spectrum was measured by TOF-SIMS in a similar way while cutting out gradually the surface of the capsule structure by ion sputtering, and it was found that all the surface was constituted by a homopolymer of polyhydroxyoctanoate. Thereby it was found that the capsule structure of this Comparative Example was a capsule structure with hydrophilic inorganic particles directly covered with a homopolymer of hydrophobic polyhydroxyoctanoate.

In addition, the molecular weight of the PHA was examined by gel permeation chromatography (GPC; Toso HLC-8020, column; Polymer laboratory PL gel MIXED-C (5 μm), solvent; chloroform, column temperature; 40° C., polystyrene equivalent) to obtain the result of Mn=21,000 and Mw=41,000. In addition, according to the laser light scattering method, the micro-capsulated pigment was monodispersed with the average particle size of 169 nm.

Then, this micro-capsulated pigment was used to prepare an oil-based ink. The composition of the black ink is as follows. Furthermore, the amount of each component shown below refers to parts by mass. A dispersing stirrer (TK Homodisper 20 manufactured by Tokushu Kika Kogyo Co., Ltd.) was used to carry out dispersion for 3 hours. For a solvent, propylene glycol monomethyl ether acetate was used.

Micro-capsulated pigment: 30 parts;
Glycerin: 6 parts;
Diethylene glycol: 7 parts;
Polyoxyethylene dodecyl ether: 0.2 parts; and
Solvent: remainder.

EXAMPLE 9

Preparation of Oil-Based Pigment Ink Using Inorganic Pigment 2

Red oxide as an inorganic red pigment was dispersed by a sand mill so that the size was 0.3 μm or smaller, and the particle size was uniformed by a settling process. When the average particle size of this pigment was measured by a laser light scattering method, it was monodispersed with the size of 152 nm. 10 parts by mass of crude enzyme of PHA synthesizing enzyme (10 U/ml) originating from P161 and 39 parts by weigh of PBS were added to one part by mass of this pigment, and were gently shaken at 30° C. for 30 minutes to absorb the PHA synthesizing enzyme to the surface of the pigment. This was subjected to centrifugation (10,000×g, 4° C., 10 minutes), the precipitate was suspended in the PBS solution, and centrifugation (10,000×g, 4° C., 10 minutes) was carried out again to obtain a fixed enzyme.

The above fixed enzyme was suspended in 48 parts by mass of 0.1 M phosphate buffer (pH 7.0), and one part by mass of (R)-3-hydroxypimelyl CoA (prepared by the process described in J. Bacteriol., 182, 2753–2760 (2000)) and 0.1 parts by mass of bovine serum albumin (manufactured by Sigma Co., Ltd.) were added therein, and were gently shaken at 37° C. for 5 minutes. Then, a 0.1 M phosphate buffer (pH 7.0) containing one part by mass of (R)-3-hydroxyoctanoyl CoA (prepared by the process described in Eur. J. Biochem., 250, 432–439 (1997)) and 0.1 parts by mass of bovine serum albumin (manufactured by Sigma Co., Ltd.) was added in this solution in the rate of 4 parts per minute using a micro tube pump (MP-3N manufactured by Tokyo Rikakikai Co., Ltd.) while the solution was gently shaken at 37° C.

After 25 minutes, the reaction solution was subjected to centrifugation (10,000×g, 4° C., 10 minutes), and precipitated particles were dried under reduced pressure to obtain a micro-capsulated pigment.

The weight of the polymer formed on the surfaces of this micro-capsulated pigment was measured by a time-of-flight secondary ion mass spectrometer (TOF-SIMS IV, manufactured by CAMECA Co., Ltd.). From the obtained mass spectrum, it was found that the surface of the micro-capsulated pigment was constituted by a copolymer of polyhydroxyoctanoate and polyhydroxypimelate (molar ratio 15:1). In addition, the mass spectrum was measured by TOF-SIMS in a similar way while cutting gradually the surface of the micro-capsulated pigment by ion sputtering, and it was found that the ratio of polyhydroxyoctanoate in the above described copolymer gradually decreased as the surface was cut, and the polymer finally changed to a homopolymer of polyhydroxypimelate. From this fact, it has been found that the micro-capsulated pigment of this Example is a micro-capsulated pigment in which a hydrophilic pigment is covered with polyhydroxypimelate having a hydrophilic functional group, which is then covered with a copolymer of polyhydroxyoctanoate and polyhydroxypimelate, with the ratio of hydrophobic polyhydroxyoctanoate being increased as the surface is approached.

In addition, the molecular weight of the PHA was examined by gel permeation chromatography (GPC; Toso HLC-8020, column; Polymer laboratory PL gel MIXED-C (5 μm), solvent; chloroform, column temperature; 40° C., polystyrene equivalent) to obtain the result of Mn=20,000 and Mw=39,000. In addition, according to the laser light scattering method, the micro-capsulated pigment was monodispersed with the average particle size of 171 nm.

Then, this micro-capsulated pigment was used to prepare an oil-based ink. The composition of the ink is as follows. Furthermore, the amount of each component shown below refers to parts by mass. A dispersing stirrer (TK Homodisper 20 manufactured by Tokushu Kika Kogyo Co., Ltd.) was used to carry out dispersion for 3 hours. For a solvent, propylene glycol monomethyl ether acetate was used.

Micro-capsulated pigment: 30 parts;
Glycerin: 6 parts;
Diethylene glycol: 7 parts;
Polyoxyethylene dodecyl ether: 0.2 parts; and
Solvent: remainder.

Comparative Example 10

Red oxide as an inorganic red pigment was dispersed by a sand mill so that the size was 0.3 μm or smaller, and the particle size was uniformed by a settling process. When the average particle size of this pigment was measured by a laser light scattering method, it was monodispersed with the size of 152 nm. This was used to prepare an oil-based ink. The composition of the ink is as follows. Furthermore, the amount of each component shown below refers to parts by mass. A dispersing stirrer (TK Homodisper 20 manufactured by Tokushu Kika Kogyo Co., Ltd.) was used to carry out dispersion for 3 hours. For a solvent, propylene glycol monomethyl ether acetate was used.

Red oxide: 30 parts;
Glycerin: 6 parts;
Diethylene glycol: 7 parts;
Polyoxyethylene dodecyl ether: 0.2 parts; and
Solvent: remainder.

EXAMPLE 10

Evaluation of Oil-Based Inks of Example 8 and Example 9 and Comparative Example 10

Dispersion stability was evaluated for the oil-based inks of Example 8, Example 9 and Comparative Example 10 in a same way as Example 4. As a result, the inks of Example 8 and Example 9 were excellent in dispersion stability with phase separation of 0%, but the oil-based ink of Comparative Example 10 was inferior in dispersion stability with phase separation of 30%, compared to those of Example 8 and Example 9.

Then, the oil-based inks of Example 8, Example 9 and Comparative Example 10 were vigorously stirred by a vortex mixer for 5 minutes to evaluate their dispersion stability in a same manner as Example 4. As a result, the ink of Example 9 was excellent in dispersion stability with phase separation of 0%, but the oil-based ink of Example 8 was slightly inferior in dispersion stability with phase separation Of 10%. The oil-based ink of Comparative Example 10 was poor in dispersion stability with phase separation of 25%.

In addition, when the micro-capsulated pigment of Examples 8 and 9 subjected to stirring were observed by an optical microscope after they were stored, each pigment particle was suitably dispersed for Example 9, while for Example 8, some pigment particles were coagulated and there existed capsule structure from which covering PHA was stripped.

From the above described fact, it has been found that an inorganic pigment is covered with PHA having a hydrophilic functional group with high affinity for the inorganic pigment, and the PHA is covered with a copolymer of hydrophilic PHA monomer unit and hydrophobic PHA monomer unit, with the ratio of the hydrophobic PHA monomer unit being increased as the surface is approached, whereby a hydrophobic PHA capsule capable of encapsulating the inorganic pigment more stably can be prepared.

EXAMPLE 11

Preparation and Evaluation of Micro-Capsulated Pigment

The PHA synthesizing enzyme derived from pYN2-C1 recombinant strain was fixed to the carbon black in the same manner as in Example 1. Then, (R,S)-3-hydroxy-5-phenoxyvaleryl CoA and (R,S)-3-hydroxy-7,8-epoxyoctanoyl CoA prepared in Reference Example 3 were added so that the final concentrations were 4 mM and 1 mM, respectively. A synthesis reaction was carried out by incubating the resulting solution at 37° C. for 30 minutes.

A part of the reaction solution was collected by centrifugation (10,000×g, 4° C., 10 minutes) and dried under reduced pressure, and thereafter was suspended in chloroform and stirred at 60° C. for 20 hours to extract PHA constituting the shell. For this extracted solution, $^1$H-NMR analysis was carried out (Apparatus: FT-NMR: Bruker DPX 400, Measured nuclear specie: $^1$H, Solvent: heavy chloroform (containing TMS)). For the unit content (%) of each side chain unit calculated from this measurement, the content of 3-hydroxy-5-phenoxyvaleric acid unit was 83%, and the content of 3-hydroxy-7,8-epoxyoctanoic acid unit was 17%.

Operation of subjecting the above reaction solution to centrifugation (10,000×g, 4° C., 10 minutes), and suspending the precipitate in purified water was conducted three times, followed by dissolving therein hexamethylene diamine as a crosslinking agent in a ratio of 0.5 part by mass of hexamethylene diamine to one part of carbon black in the suspension. After ensuring it was dissolved, water was removed by freeze-drying (referred to as Particle 1). Particle 1 was reacted at 70° C. for 12 hours (referred to as Particle 2).

The above Particles 1 and 2 were suspended in chloroform, and was stirred at 60° C. for 20 hours to extract PHA constituting the shell, and chloroform was removed by drying under reduced pressure, followed by carrying out measurements using a differential scanning calorimeter (DSC; Pyris 1 manufactured by PerkinElmer Co., Ltd., rate of temperature rise: 10° C./minute). As a result, for Particle 1, a clear exothermic peak was observed near 90° C., showing that reaction between an epoxy group in the polymer and hexamethylene diamine occurred and crosslinking between polymers progressed. For Particle 2, on the other hand, a clear heat flow was not found, showing that the crosslinking reaction was almost completed.

In addition, infrared absorption was measured for a similar sample (FT-IR; 1720X manufactured by PerkinElmer Co., Ltd.). As a result, the peaks of amine (near 3340 cm$^{-1}$) and epoxy (near 822 cm$^{-1}$) found for Particle 1 disappeared for Particle 2.

From the above results, it has been apparent that a crosslinked polymer can be obtained by reacting PHA having an epoxy unit on the side chain with hexamethylene diamine.

On the other hand, a sample was prepared and examined in a same manner as described above except that (R)-3-hydroxyoctanoyl CoA was used instead of (R,S)-3-hydroxy-7,8-epoxyoctanoyl CoA, but a result clearly showing crosslinking between polymers as described above was not obtained.

The above Particle 2 was resuspended in ethanol, followed by collecting the micro-capsulated pigment of Particle 2 again by centrifugation operation.

The above described macro-capsulated pigment was suspended in hexane, methanol, propylene glycol monomethyletheracetate or ethylether, and was stored at a room temperature for 30 days, but no substantial change was found in any of these solvents, showing that the micro-capsulated pigment had satisfactory chemical resistance. Thus, it has been found that the micro-capsulated pigment is capable of being used in many types of dispersion media. Also, the above described electrophoretic particle had satisfactory mechanical strength and heat resistance.

EXAMPLE 12

Preparation and Evaluation of Water-Based Pigment Ink

A water-based black ink was prepared in a same manner as Example 4 except that the micro-capsulated pigment prepared in the above described Example 11 was used instead of the black micro-capsulated pigment prepared in Example 1. In addition, a water-based pigment ink of Comparative Example was prepared in a same manner as Example 4.

For the above described water-based inks, the dispersion stability and average particle size were evaluated in a same manner as Example 4. As a result, for the ink prepared from the micro-capsulated pigment of Example 11, the phase separation was 0%, and the average particle size was 179 nm immediately after preparation, and 188 nm after storage. On the other hand, for the ink of Comparative Example, the phase separation was 25%, and the average particle size was 289 nm immediately after preparation, and 1865 nm after storage.

Therefore, for the ink prepared from the micro-capsulated pigment of Example 11, the particle size of the micro-capsulated pigment was not significantly changed even after the ink was produced as a water-based recording liquid, and the dispersion stability was excellent. This is particularly a useful effect in uses of inks for ink jet printers such that ink is discharged from very small nozzles for trajectory recording.

EXAMPLE 13

Evaluation as an Ink for Ink Jet Printers

The ink was evaluated as an ink for ink jet printers in a same manner as Example 5 except that the ink of the above described Example 12 was used instead of the ink prepared in Example 4.

As a result, when the ink of Example 12 was used, the OD was 1.46, the dot diameter was 68 $\mu$m, the edge of line was neatly drawn in line form for the dot periphery shape, white decolored portions were not found for the solid uniformity, almost no pattern was seen through the medium, and the optical density measured by a Macbeth densitometer was smaller than 0.2 for the strike-through property, and almost all dots were close to circles from a statistical viewpoint for the circularity.

From the above results, the ink prepared from the micro-capsulated pigment of Example 11 is used as an ink for ink jet printers, whereby a coagulated pigment on the recording medium (paper) is dispersed uniformly in ink dots in the form of fine particles, thus making it possible to obtain ink dots excellent in peripheral and outer shapes, having appropriately widened dot diameters, having uniform distribution of image density in dots, and being almost free from feathering.

EXAMPLE 14

Preparation and Evaluation of Oil-Based Pigment Ink

An oil-based black ink was prepared in a same manner as Example 6 except that the micro-capsulated pigment prepared in the above described Example 11 was used instead of the black micro-capsulated pigment prepared in Example 1, and propylene glycol monomethyl ether acetate or ethyl ether was used as a solvent. In addition, an oil-based pigment ink of Comparative Example was prepared in a same manner as Example 6.

When the above described black inks were compared to each other, no difference was found for the size of pigment particles in the ink and dispersion stability, but the viscosity of Comparative Example was higher than that of the latter. That is, it has been found that the pigment ink of the present invention has good dispersion stability even though a synthetic resin such as rosin phenol resin or ketone resin that is usually added in an oil-based pigment ink as a dispersion stabilizing resin is not added. This is particularly a useful effect in use of pens such as an oil-based sign pen and an oil-based marker, and oil-based recording liquids such as a printing ink, because the pigment density is relatively increased and the color rendering property is improved.

In addition, the above described black ink was stored at a room temperature for 30 days, but the black ink using the micro-capsulated pigment prepared in Example 11 could be used without trouble, and therefore it was found that the micro-capsulated pigment also has satisfactory storage stability in various solvents.

EXAMPLE 15

Preparation of Micro-Capsulated Pigment

A PHA synthesizing enzyme originating from the pYN2-C1 recombination strain was fixed to carbon black in a same manner as Example 1. Then, (R,S)-3-hydroxy-5-phenoxyvaleril CoA and (R,S)-3-hydroxy-7,8-epoxyoctanoyl CoA prepared in Reference Example 3 was added so that the final concentrations were 4 mM and 1 mM, respectively. A synthesis reaction was carried out by incubating the resulting solution at 37° C. for 30 minutes. The produced micro-capsulated pigment was filtered, washed and dried, and 10 parts by mass of terminal amino modified polysiloxane (modified silicone oil TSF 4700 manufactured by GE Toshiba Silicone Co., Ltd.) were added to one part by mass of the micro-capsulated pigment, and was reacted at 70° C. for 2 hours. Operation of suspending this in methanol and subjecting to centrifugation (10,000×g, 4° C., 20 minutes) was repeatedly conducted to carry out washing and drying, whereby a micro-capsulated pigment having a graft chain of polysiloxane was obtained.

Furthermore, the above described micro-capsulated pigment had satisfactory mechanical strength, whether resistance and heat resistance.

EXAMPLE 16

Preparation and Evaluation of Water-Based Pigment Ink

A water-based black ink was prepared in a same manner as Example 4 except that the micro-capsulated pigment prepared in the above described Example 15 was used instead of the black micro-capsulated pigment prepared in Example 1. In addition, a water-based pigment ink of Comparative Example was prepared in a same manner as Example 4.

For the above described water-based inks, the dispersion stability and average particle size were evaluated in a same manner as Example 4. As a result, for the ink prepared from the micro-capsulated pigment of Example 15, the phase separation was 0%, and the average particle size was 177 nm immediately after preparation, and 182 nm after storage. On the other hand, for the ink of Comparative Example, the phase separation was 25%, and the average particle size was 289 nm immediately after preparation, and 1865 nm after storage.

Therefore, for the ink prepared from the micro-capsulated pigment of Example 15, the particle size of the micro-capsulated pigment was not significantly changed even after the ink was produced as a water-based recording liquid, and the dispersion stability was excellent. This is particularly a useful effect in uses of inks for ink jet printers such that ink is discharged from very small nozzles for trajectory recording.

EXAMPLE 17

Evaluation As An Ink for Ink Jet Printers

The ink was evaluated as an ink for ink jet printers in a same manner as Example 5 except that the ink of the above described Example 16 was used instead of the ink prepared in Example 4.

As a result, when the ink of Example 16 was used, the OD was 1.47, the dot diameter was 71 $\mu$m, the edge of line was neatly drawn in line form for the dot periphery shape, white decolored portions were not found for the solid uniformity, almost no pattern was seen through the medium, and the optical density measured by a Macbeth densitometer was smaller than 0.2 for the strike-through property, and almost all dots were close to circles from a statistical viewpoint for the circularity.

From the above described results, the ink prepared from the micro-capsulated pigment of Example 15 is used as an ink for ink jet printers, whereby a coagulated pigment on the recording medium (paper) is dispersed uniformly in ink dots in the form of fine particles, thus making it possible to obtain ink dots excellent in peripheral and outer shapes, having appropriately widened dot diameters, having uniform distribution of image density in dots, and being almost free from feathering.

The micro-capsulated pigment contained in the pigment ink of the present invention exhibits satisfactory dispersibility in the absence of surfactant in water-based, oil-based and both water and oil-based compositions by appropriately selecting the composition of PHA, and due to the reduced particle size, the micro-capsulated pigment is excellent in density, fineness, transparency, coloring and color rendering properties, and has excellent dispersibility and dispersion stability with time. The pigment ink of the present invention can easily be produced as pens such as a water-based ball point pen, a fountain pen, a water-based sign pen and a water-based maker, and a water-based ink for on-demand type inkjet printers such as babble jet system, thermal jet system and piezo system ink jet printers, as well as pens such as an oil-based sign pen and an oil-based marker, and oil-based inks such as print ink. This pigment ink has an advantage that the amount of dispersant can be reduced, thereby making it possible to reduce viscosity, increase the concentration of pigment, and improve the color rendering property.

What is claimed is:

1. A pigment ink containing a color material with at least part of surfaces of pigment particles covered with polyhydroxyalkanoate, and a medium for dispersion of the color material, wherein said polyhydroxyalkanoate comprised of at least one selected from the group consisting of monomer units expressed by Formulas [1] to [10]:

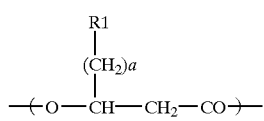

[1]

(wherein symbol "a" represents an integer, and the combination of R1 and "a" is selected from the group consisting of a combination of a hydrogen atom and any one integer selected from the group consisting of 0 to 10;

a combination of a halogen atom and any one integer selected from the group consisting of 1 to 10;

a combination of a chromophoric group and any one integer selected from the group consisting of 1 to 10;

a combination of a carboxyl group or a salt thereof and any one integer selected from the group consisting of 0 to 10; and a combination of

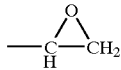

and any one integer selected from the group consisting of 1 to 7),

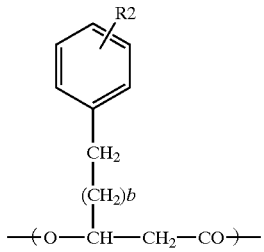

[2]

(wherein b represents any one integer selected from the group consisting of 0 to 7, and R2 is selected from the group consisting of a hydrogen atom (H), a halogen atom, —CN, —NO$_2$, —CF$_3$, —C$_2$F$_5$ and —C$_3$F$_7$),

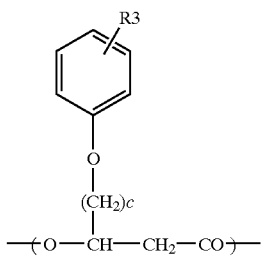

[3]

(wherein c represents any one integer selected from the group consisting of 1 to 8, and R3 is selected from the group consisting of a hydrogen atom (H), a halogen atom, —CN, —$NO_2$, —$CF_3$, —$C_2F_5$ and —$C_3F_7$),

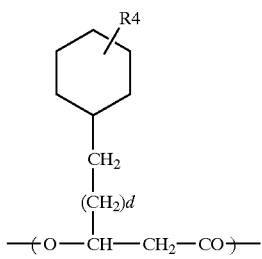

[4]

(wherein d represents any one integer selected from the group consisting of 0 to 7, and R4 is selected from the group consisting of a hydrogen atom (H), a halogen atom, —CN, —$NO_2$, —$CF_3$, —$C_2F_5$ and —$C_3F_7$),

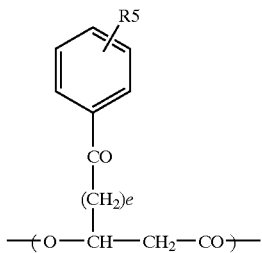

[5]

(wherein e represents any one integer selected from the group consisting of 1 to 8, and R5 is selected from the group consisting of a hydrogen atom (H), a halogen atom, —CN, —$NO_2$, —$CF_3$, —$C_2F_5$, $C_3F_7$, —$CH_3$, —$C_2H_5$ and —$C_3H_7$),

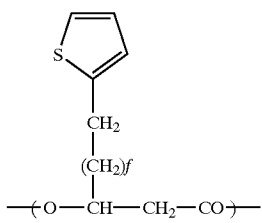

[6]

(wherein f represents any one integer selected from the group consisting of 0 to 7),

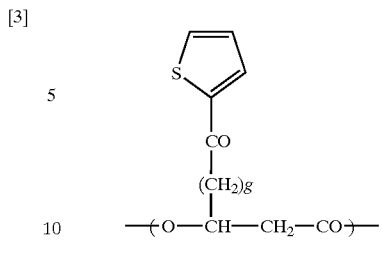

[7]

(wherein g represents any one integer selected from the group consisting of 1 to 8),

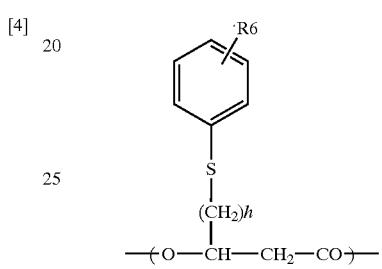

[8]

(wherein h represents any one integer selected from the group consisting of 1 to 7, and R6 is selected from the group consisting of a hydrogen atom (H), a halogen atom, —CN, —$NO_2$, —COOR', —$SO_2R"$, —$CH_3$, —$C_2H_5$, —$C_3H_7$, —$CH(CH_3)_2$ and —$C(CH_3)_3$, wherein R' is selected from the group consisting of a hydrogen atom (H), Na, K, —$CH_3$ and —$C_2H_5$, and R" is selected from the group consisting of —OH, ONa, —OK, a halogen atom, —$OCH_3$ and —$OC_2H_5$),

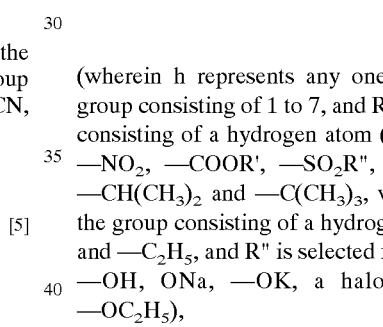

[9]

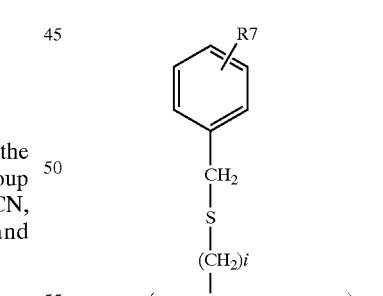

(wherein i represents any one integer selected from the group consisting of 1 to 7, and R7 is selected from the group consisting of a hydrogen atom (H), a halogen atom, —CN, —$NO_2$, —COOR' and —$SO_2R"$, wherein R' is selected from the group consisting of a hydrogen atom (H), Na, K, —$OH_3$ and —$C_2H_5$, and R" is selected from the group consisting of —OH, —ONa, —OK, a halogen atom, —$OCH_3$ and —$OC_2H_5$), and

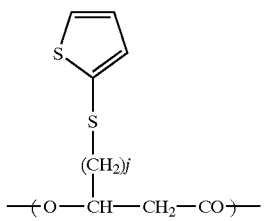

[10]

(wherein j represents any one integer selected from the group consisting of 1 to 9).

2. A pigment ink containing a color material with at least part of surfaces of pigment particles covered with polyhydroxyalkanoate, and a medium for dispersion of the color material,
wherein the polyhydroxyalkanoate has a hydrophilic functional group, an anionic functional group, and a carboxyl group; and
wherein said carboxyl group is introduced by at least one monomer unit selected from the group consisting of the monomer unit expressed by Formula [11]:

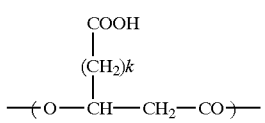

[11]

(wherein k represents any one integer selected from the group consisting of 1 to 10.).

3. The pigment ink according to claim 1, wherein a monomer unit composition of said polyhydroxyalkanoate as changed in the direction of from an inside of said color material to an outside thereof.

4. The pigment ink according to claim 1, wherein at least a part of said polyhydroxyalkanoate is chemically modified.

5. The pigment ink according to claim 4, wherein said chemically modified polyhydroxyalkanoate has at least a graft chain.

6. The pigment ink according to claim 5, wherein said graft chain is formed by chemical modification of polyhydroxyalkanoate containing at least a monomer unit having an epoxy group.

7. The pigment ink according to claim 6, wherein said graft chain is a graft chain of compounds each of which has an amino group.

8. The pigment ink according to claim 7, wherein said compound having an amino group is an amino-terminal-modified compound.

9. The pigment ink according to claim 8, wherein each of said amino-terminal-modified compounds is independently selected from the group consisting of polyvinyl amine, polyethylene imine and amino-terminal-modified polysiloxane.

10. The pigment ink according to claim 4, wherein at least a part of said polyhydroxyalkanoate is crosslinked.

11. The pigment ink according to claim 10, wherein said crosslinked polyhydroxyalkanoate is a polyhydroxyalkanoate in which a polyhydroxyalkanoate containing at least a monomer unit having an epoxy group is crosslinked.

12. The pigment ink according to claim 11, wherein said crosslinked polyhydroxyalkanoate is a polyhydroxyalkanoate crosslinked with at least one selected from the group consisting of a diamine compound, succinic anhydride, 2-ethyl-4-methylimidazole and irradiation of electron ray.

13. The pigment ink according to claim 12, wherein said diamine compound is hexamethylenediamine.

14. A process for preparing a pigment ink containing a color material with at least part of surfaces of pigment particles covered with polyhydroxyalkanoate, and a medium for dispersion of the color material, comprising the step of:

carrying out a polyhydroxyalkanoate synthesis reaction with 3-hydroxyacyl CoA as a substrate in the presence of a polyhydroxyalkanoate synthesizing enzyme fixed on the surfaces of pigment particles dispersed in an aqueous medium, thereby at least part of the surface of the pigment particle is covered with polyhydroxyalkanoate to obtain the color material, and dispersing the color material in the medium for dispersions wherein said polyhydroxyalkanoate is comprised of at least one selected from the group consisting of monomer units expressed by Formulas [1] to [10]:

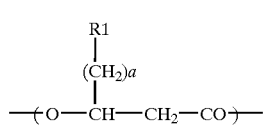

[1]

(wherein symbol "a" represents an integer, and the combination of R1 and "a" is selected from the group consisting of a combination of a hydrogen atom and any one integer selected from the group consisting of 0 to 10;

a combination of a halogen atom and any one integer selected from the group consisting of 1 to 10;

a combination of a chromophoric group and any one integer selected from the group consisting of 1 to 10;

a combination of a carboxyl group or a salt thereof and any one integer selected from the group consisting of 1 to 10; and a combination of

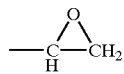

and any one integer selected from the group consisting of 1 to 7),

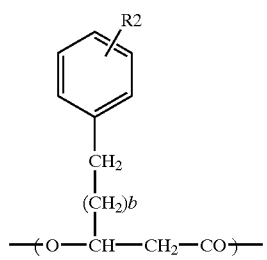

[2]

(wherein b represents any one integer selected from the group consisting of 0 to 7, and R2 is selected from the group consisting of a hydrogen atom (H), a halogen atom, —CN, —NO$_2$, —CF$_3$, —C$_2$F$_5$ and —C$_3$F$_7$),

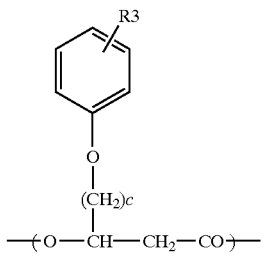

[3]

(wherein c represents any one integer selected from the group consisting of 1 to 8, and R3 is selected from the group consisting of a hydrogen atom (H), a halogen atom, —CN, —NO$_2$, —CF$_3$, —C$_2$F$_5$ and —C$_3$F$_7$),

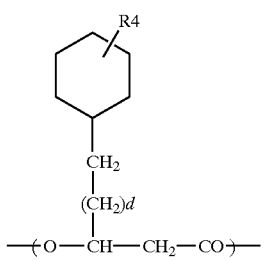

[4]

(wherein d represents any one integer selected from the group consisting of 0 to 7, and R4 is selected from the group consisting of a hydrogen atom (H), a halogen atom, —CN, —NO$_2$, —CF$_3$, —C$_2$F$_5$ and —C$_3$F$_7$),

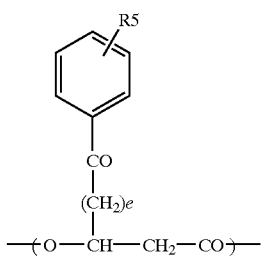

[5]

(wherein e represents any one integer selected from the group consisting of 1 to 8, and R5 is selected from the group consisting of a hydrogen atom (H), a halogen atom, —CN, —NO$_2$, —CF$_3$, —C$_2$F$_5$, C$_3$F$_7$, —CH$_3$, —C$_2$H$_5$ and —C$_3$H$_7$),

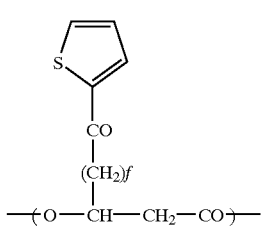

[6]

(wherein f represents any one integer selected from the group consisting of 0 to 7),

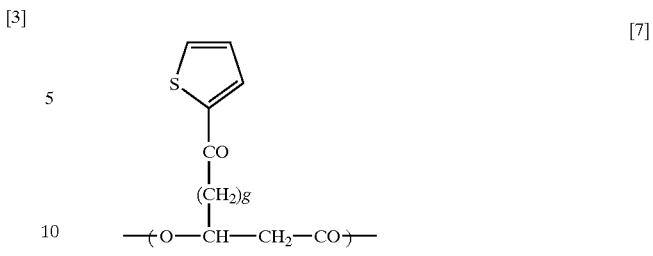

[7]

(wherein g represents any one integer selected from the group consisting of 1 to 8),

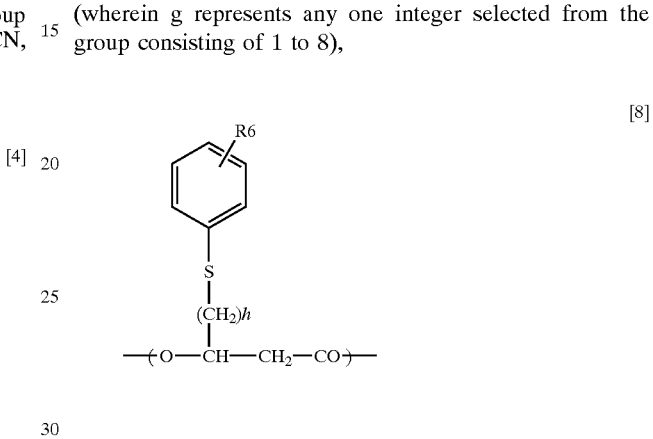

[8]

(wherein h represents any one integer selected from the group consisting of 1 to 7, and R6 is selected from the group consisting of a hydrogen atom (H), a halogen atom, —CN, —NO$_2$, —COOR', SO$_2$R", —CH$_3$, —C$_2$H$_5$, —C$_3$H$_7$, —CH(CH$_3$)$_2$ and —C(CH$_3$)$_3$, wherein R' is selected from the group consisting of a hydrogen atom (H), Na, K, —CH$_3$ and —C$_2$H$_5$, and R" is selected from the group consisting of —OH, ONa, —OK, a halogen atom, —OCH$_3$ and —OC$_2$H$_5$),

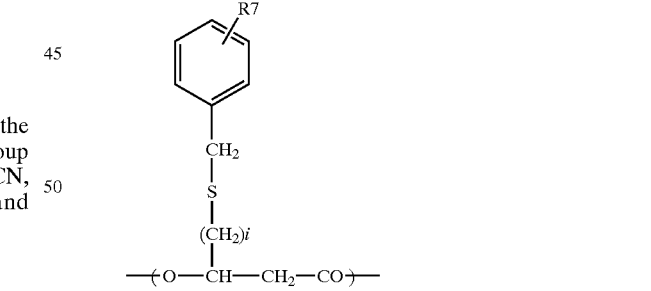

[9]

(wherein i represents any one integer selected from the group consisting of 1 to 7, and R7 is selected from the group consisting of a hydrogen atom (H), a halogen atom, —CN, —NO$_2$, —COOR' and —SO$_2$R", wherein R' is selected from the group consisting of a hydrogen atom (H), Na, K, —CH$_3$ and —C$_2$H$_5$, and R" is selected from the group consisting of —OH, —ONa, —OK, a halogen atom, —OCH$_3$ and —OC$_2$H$_5$),

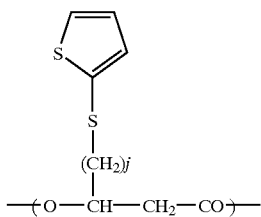

[10]

(wherein j represents any one integer selected from the group consisting of 1 to 9).

15. The process according to claim 14, wherein each corresponding 3-hydroxyacyl CoA is selected from the group consisting of 3-hydroxyacyl CoA expressed by formulas [12] to [21]:

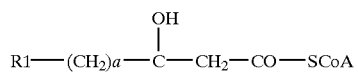

[12]

(wherein —SCoA represents a CoA bound to alkanoic acid, symbol "a" represents an integer, and the combination of R1 and a is selected from the group consisting of a combination of a hydrogen atom (H) and any one integer selected from the group consisting of 0 to 10;

- a combination of a halogen atom and any one integer selected from the group consisting of 1 to 10;
- a combination of a chromophoric group and any one integer selected from the group consisting of 1 to 10;
- a combination of a carboxyl group or a salt thereof and any one integer selected from the group consisting of 1 to 10; and
- a combination of

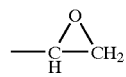

and any one integer selected from the group consisting of 1 to 7), and corresponds to R1 and a in the monomer unit expressed by said Formula [1],

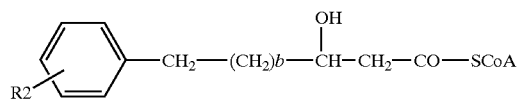

[13]

(wherein —SCoA represents a CoA bound to alkanoic acid, b represents any one integer selected from the group consisting of 0 to 7 corresponding to b in the monomer unit expressed by the above described Formula [2], and R2 is selected from the group consisting of a hydrogen atom (H), halogen atom, —CN, —NO$_2$, —CF$_3$, —C$_2$F$_5$ and —C$_3$F$_7$ corresponding to R2 in the monomer unit expressed by the above described Formula [2]),

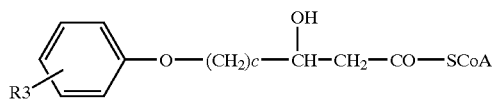

[14]

(wherein —SCoA represents a CoA bound to alkanoic acid, c represents any one integer selected from the group consisting of 1 to 8 corresponding to c in the monomer unit expressed by the above described Formula [3], and R3 is selected from the group consisting of a hydrogen atom (H), halogen atom, —CN, —NO$_2$, —CF$_3$, —C$_2$F$_5$ and —C$_3$F$_7$ corresponding to R3 in the monomer unit expressed by the above described Formula [3]),

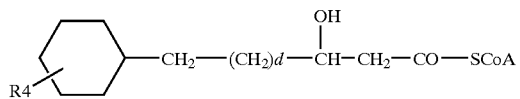

[15]

(wherein —SCoA represents a CoA bound to alkanoic acid, d represents any one integer selected from the group consisting of 0 to 7 corresponding to d in the monomer unit expressed by the above described Formula [4], and R4 is selected from the group consisting of a hydrogen atom (H), halogen atom, —CN, —NO$_2$, —CF$_3$, —C$_2$F$_5$ and —C$_3$F$_7$ corresponding to R4 in the monomer unit expressed by the above described Formula [4]),

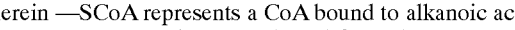

[16]

(wherein —SCoA represents a CoA bound to alkanoic acid, e represents any one integer selected from the group consisting of 1 to 8 corresponding to e in the monomer unit expressed by the above described Formula [5], is selected from the group consisting of a hydrogen atom (H), halogen atom, —CN, —NO$_2$, —CF$_3$, —C$_2$F$_5$, —C$_3$F$_7$, —CH$_3$, —C$_2$H$_5$ and —C$_3$H$_7$ corresponding to R5 in the monomer unit expressed by the above described Formula [5]),

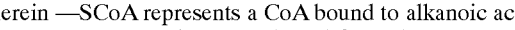

[17]

(wherein —SCoA represents a CoA bound to alkanoic acid, and f represents any one integer selected from the group consisting of 0 to 7 corresponding to f in the monomer unit expressed by the above described Formula [6]),

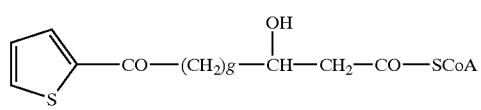

[18]

(wherein —SCoA represents a CoA bound to alkanoic acid, and g represents any one integer selected from the group consisting of 1 to 8 corresponding to g in the monomer unit expressed by the above described Formula [7]),

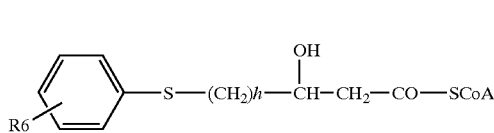
[19]

(wherein —SCoA represents a CoA bound to alkanoic acid, h represents any one integer selected from the group consisting of 1 to 7 corresponding to h in the monomer unit expressed by the above described Formula [8], and R6 is selected from the group consisting of a hydrogen atom (H), halogen atom, —CN, —$NO_2$, —COOR', —$SO_2R''$, —$CH_3$, —$C_2H_5$, —$C_3H_7$, —$CH(CH_3)_2$ and —$C(CH_3)_3$ corresponding to R6 in the monomer unit expressed by the above described Formula [8] wherein R' is selected from the group consisting of a hydrogen atom (H), Na, K, —$CH_3$ and —$C_2H_5$, and R" is selected from the group consisting of —OH, —ONa, —OK, a halogen atom, —$OCH_3$ and —$OC_2H_5$),

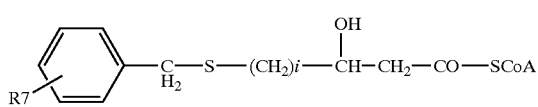
[20]

(wherein —SCoA represents a CoA bound to alkanoic acid, i represents any one integer selected from the group consisting of 1 to 7 corresponding to i in the monomer unit expressed by the above described Formula [9], and R7 is selected from the group consisting of a hydrogen atom (H), halogen atom, —CN, —$NO_2$, —COOR' and —$SO_2R''$ corresponding to R7 in the monomer unit expressed by the above described Formula [9] wherein R' is selected from the group consisting of a hydrogen atom (H), Na, K, —$CH_3$ and —$C_2H_5$, and R" represents any of —OH, —ONa, —OK, a halogen atom, —$OCH_3$ and —$OC_2H_5$), and

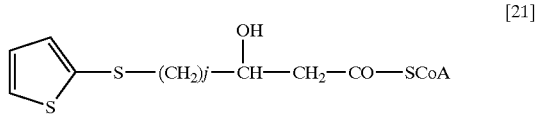
[21]

(wherein —SCoA represents a CoA bound to alkanoic acid, and j represents any one integer selected from the group consisting of 1 to 9 corresponding to j in the monomer unit expressed by the above described Formula [10]).

16. A process for preparing a pigment ink containing a color material with at least part of surfaces of pigment particles covered with polyhydroxyalkanoate, and a medium for dispersion of the color material, comprising the step of:
carrying out a polyhydroxyalkanoate synthesis reaction with 3-hydroxyacyl CoA as a substrate in the presence of a polyhydroxyalkanoate synthesizing enzyme fixed on the surfaces of pigment particles dispersed in an aqueous medium, thereby at least part of the surface of the pigment particle is covered with polyhydroxyalkanoate to obtain the color material, and dispersing the color material in the medium for dispersion,
wherein the polyhydroxyalkanoate has a hydrophilic functional group, an anionic functional group, and a carboxyl group; and wherein said carboxyl group is introduced by at least one of monomer units selected from the group consisting of the monomer unit expressed by Formula [11];

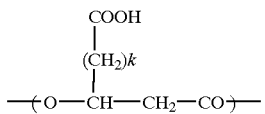
[11]

(wherein k represents any one integer selected from the group consisting of 1 to 10.).

17. The process according to claim 15, wherein the composition of said 3-hydroxyacyl CoA is changed with time, whereby the composition of 3-hydroxyalkanoic acid unit of said polyhydroxyalkanoate is changed in the direction of from an inside of said electrophoretic particle to an outside thereof.

18. The process according to claim 15, which process further comprises a step of chemically modifying at least a part of polyhydroxyalkanoate with which said pigment particles are covered.

19. The process according to claim 18, wherein said chemically modifying step is a step of adding a graft chain to at least a part of polyhydroxyalkanoate.

20. The process according to claim 19, wherein said step of adding a graft chain is a step of reacting at least a part of polyhydroxyalkanoate with a compound having a reactive functional group at the terminal.

21. The process according to claim 20, wherein said polyhydroxyalkanoate contains at least a monomer unit having an epoxy group.

22. The process according to claim 20 or 21, wherein said compound having a reactive functional group at the terminal has an amino group.

23. The process according to claim 22, wherein said compound having an amino group is an amino-terminal-modified compound.

24. The process according to claim 23, wherein said amino-terminal-modified compound is selected from the group consisting of polyvinyl amine, polyethylene imine and amino-terminal-modified polysiloxane.

25. The process according to claim 18, wherein said chemically modifying step is a step of crosslinking at least a part of polyhydroxyalkanoate.

26. The process according to claim 25, wherein said crosslinking step is a step of reacting at least a part of polyhydroxyalkanoate with a crosslinking agent.

27. The process according to claim 26, wherein said polyhydroxyalkanoate contains at least a monomer unit having an epoxy group.

28. The process according to claim 26 or 27, wherein said crosslinking agent is at least one selected from the group consisting of a diamine compound, succinic anhydride and 2-methyl-4-methylimidazole.

29. The process according to claim 28, wherein said diamine compound is hexamethylene diamine.

30. The process according to claim 25, wherein said crosslinking step is a step of irradiating polyhydroxyalkanoate with electron rays.

31. The process according to any one of claim 14, 15 or 16, wherein the polyhydroxyalkanoate synthesizing enzyme is produced by a microorganism capable of producing the enzyme or a transformant having a gene associated with the production capability introduced in a host microorganism.

32. The process according to claim 31, wherein the microoraganism capable of producing polyhydroxyalkanoate synthesizing enzyme is a microorganism belonging to *Pseudomonas* sp.

33. The process according to claim 32, wherein the microorganism capable of producing polyhydroxyalkanoate synthesizing enzyme is at least one microorganism selected from the group consisting of *Pseudomonas putida* P91 (FERM BP-7373), *Pseudomonas cichorii* H45 (FERM BP-7374), *Pseudomonas cichorii* YN2 (FERM BP-7375) and *Pseudomonas jessenii* P161 (FERM BP-7376).

34. The process according to claim 31, wherein the microorganism capable of producing polyhydroxyalkanoate synthesizing enzyme is a microorganism belonging to *Burkholderia* sp.

35. The process according to claim 34, wherein the microorganism capable of producing polyhydroxyalkanoate synthesizing enzyme is at least one microorganism selected from the group consisting of *Burkholderia cepacia* KK01 (FERM BP-4235), *Burkholderia* sp. OK3 (FERM P-17370) and *Burkholderia* sp. OK4 (FERM P-17371).

36. The process according to claim 31, wherein the microorganism capable of producing polyhydroxyalkanoate synthesizing enzyme is a microorganism belonging to *Alcaligenes* sp.

37. The process according to claim 36, wherein the microorganism capable of producing polyhydroxyalkanoate synthesizing enzyme is *Alcaligenes* sp. TL2 (FERM BP-6913).

38. The process according to claim 31, wherein the microorganism capable of producing polyhydroxyalkanoate synthesizing enzyme is a microorganism belonging to *Ralstonia* sp.

39. The process according to claim 38, wherein the microorganism capable of producing polyhydroxyalkanoate synthesizing enzyme is *Raistonia eutropha* TB64 (FERM BP-6933).

40. The process according to claim 31, wherein said host microorganism is *Escheichia coli*.

41. The pigment ink according to any one of claims 1 or 2 to 13, wherein the molecular weight of said polyhydroxyalkanoate is in the range of from 1000 to 10000000.

42. The pigment ink according to claim 41, wherein the molecular weight of said polyhydroxyalkanoate is in the range of from 3000 to 1000000.

43. The pigment ink according to claim 5, wherein said graft chain is a graft chain of compounds each of which has an amino group.

44. The pigment ink according to claim 43, wherein said compound having an amino group is a amino-terminal-modified compound.

45. The pigment ink according to claim 44, wherein each of said amino-terminal-modified compounds is independently selected from the group consisting of polyvinyl amine, polyethylene imine and amino-terminal-modified polysiloxane.

46. The pigment ink according to any of claims 43 to 45, wherein the molecular weight of said polyhydroxyalkanoate is in the range of from 1000 to 10000000.

47. The pigment ink according to claim 46, wherein the molecular weight of said polyhydroxyalkanoate is in the range of from 3000 to 1000000.

48. The pigment ink according to claim 10, wherein said crosslinked polyhydroxyalkanoate is a polyhydroxyalkanoate crosslinked with at least one selected from the group consisting of a diamine compound, succinic anhydride, 2-ethyl-4-methylimidazole and irradiation of electron ray.

49. The pigment ink according to claim 48, wherein said diamine compound is hexamethylenediamine.

50. The pigment ink according to claim 48 or 49, wherein the molecular weight of said polyhydroxyalkanoate is in the range of from 1000 to 10000000.

51. The pigment ink according to claim 50, wherein the molecular weight of said polyhydroxyalkanoate is in the range of from 3000 to 1000000.

52. The process according to claim 16, wherein a 3-hydroxyacyl CoA corresponding to the monomer unit is at least one of the 3-hydroxyacyl CoA expressed by Formula [22]:

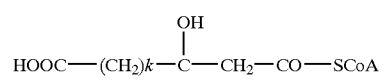

[22]

(wherein —SCoA represents a CoA bound to alkanoic acid, and k is at least integer selected from the group consisting of 1 to 10, and corresponds to k in the monomer unit expressed by said Formula [11].

* * * * *

UNITED STATES PATENT AND TRADEMARK OFFICE
CERTIFICATE OF CORRECTION

PATENT NO. : 6,916,861 B2
DATED : July 12, 2005
INVENTOR(S) : Tsuyoshi Nomoto et al.

It is certified that error appears in the above-identified patent and that said Letters Patent is hereby corrected as shown below:

Column 1,
Line 10, "either an" should read -- either a --;
Line 27, "A various" should read -- Various --; and
Line 38, "ments" should read -- ment --.

Column 2,
Line 11, "production" should read -- production of --.

Column 8,
Line 49, "no" should be deleted.

Column 15,
Line 62, "EnglanBiolab" should read -- England Biolab --.

Column 16,
Line 43, "an pigment" should read -- a pigment --.

Column 17,
Line 10, "if" should be deleted.

Column 21,
Line 9, "describe" should read -- described --.

Column 23,
Line 61, "a various" should read -- various --.

Column 24,
Line 3, "depending" should read -- depending on --.

Column 29,
Line 5, "(Amasham Pharmacia·Biotech)" should read -- (Amasham Pharmacia·Biotech). --.

Column 31,
Line 63, "bat" should read -- bath --.

Column 41,
Line 12, "Of" should read -- of --.

Column 57,
Line 38, "material." should read -- material, --; and
Line 42, "comprised" should read -- is comprised --.

UNITED STATES PATENT AND TRADEMARK OFFICE
CERTIFICATE OF CORRECTION

PATENT NO. : 6,916,861 B2
DATED : July 12, 2005
INVENTOR(S) : Tsuyoshi Nomoto et al.

It is certified that error appears in the above-identified patent and that said Letters Patent is hereby corrected as shown below:

Column 58,
Line 35, "of 0" should read -- of 1 --.

Column 61,
Line 34, "as" should read -- is --.

Column 62,
Line 16, "dispersions" should read -- dispersions, --.

Column 64,
Line 66, "–$OC_2H_5$)," should read -- –$OC_2H_5$), and --.

Column 68,
Line 3, "Formula [11];" should read -- Formula [11] --.

Column 69,
Line 34, "*Raistonia*" should read -- *Ralstonia* --; and
Line 37, "*Escheichia coli.*" should read -- *Escherichia coli.* --.

Column 70,
Line 2, "is a" should read -- is an --;
Line 42, "integer" should read -- an integer --; and
Line 44, "Formula [11]." should read -- Formula [11]). --.

Signed and Sealed this

Twenty-first Day of March, 2006

JON W. DUDAS
*Director of the United States Patent and Trademark Office*

SEQUENCE LISTING

<160> NUMBER OF SEQ ID NOS: 14

<210> SEQ ID NO 1
<211> LENGTH: 559
<212> TYPE: PRT
<213> ORGANISM: Pseudomonas cichorii YN2; FERM BP-7375

<400> SEQUENCE: 1

```
Met Ser Asn Lys Ser Asn Asp Glu Leu Lys Tyr Gln Ala Ser Glu Asn
 1               5                  10                  15

Thr Leu Gly Leu Asn Pro Val Val Gly Leu Arg Gly Lys Asp Leu Leu
             20                  25                  30

Ala Ser Ala Arg Met Val Leu Arg Gln Ala Ile Lys Gln Pro Val His
         35                  40                  45

Ser Val Lys His Val Ala His Phe Gly Leu Glu Leu Lys Asn Val Leu
     50                  55                  60

Leu Gly Lys Ser Gly Leu Gln Pro Thr Ser Asp Asp Arg Arg Phe Ala
 65                  70                  75                  80

Asp Pro Ala Trp Ser Gln Asn Pro Leu Tyr Lys Arg Tyr Leu Gln Thr
                 85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
                245                 250                 255
```

-continued

```
Asn Pro Thr Lys Glu Gln Arg Glu Trp Gly Leu Ser Thr Tyr Ile Glu
            260                 265                 270

Ala Leu Lys Glu Ala Val Asp Val Thr Ala Ile Thr Gly Ser Lys
        275                 280                 285

Asp Val Asn Met Leu Gly Ala Cys Ser Gly Gly Ile Thr Cys Thr Ala
    290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Leu Asp Ser Asp Val Ala
                325                 330                 335

Leu Phe Val Asn Glu Gln Thr Leu Glu Ala Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
                405                 410                 415

Lys Asn Asn Pro Leu Ile Arg Pro Asn Ala Leu Glu Val Cys Gly Thr
            420                 425                 430

Pro Ile Asp Leu Lys Gln Val Thr Ala Asp Ile Phe Ser Leu Ala Gly
        435                 440                 445

Thr Asn Asp His Ile Thr Pro Trp Lys Ser Cys Tyr Lys Ser Ala Gln
    450                 455                 460

Leu Phe Gly Gly Asn Val Glu Phe Val Leu Ser Ser Gly His Ile
465                 470                 475                 480

Gln Ser Ile Leu Asn Pro Pro Gly Asn Pro Lys Ser Arg Tyr Met Thr
            485                 490                 495

Ser Thr Glu Val Ala Glu Asn Ala Asp Glu Trp Gln Ala Asn Ala Thr
        500                 505                 510

Lys His Thr Asp Ser Trp Trp Leu His Trp Gln Ala Trp Gln Ala Gln
    515                 520                 525

Arg Ser Gly Glu Leu Lys Lys Ser Pro Thr Lys Leu Gly Ser Lys Ala
    530                 535                 540

Tyr Pro Ala Gly Glu Ala Ala Pro Gly Thr Tyr Val His Glu Arg
545                 550                 555

<210> SEQ ID NO 2
<211> LENGTH: 1680
<212> TYPE: DNA
<213> ORGANISM: Pseudomonas cichorii YN2; FERM BP-7375

<400> SEQUENCE: 2
atgagtaaca agagtaacga tgagttgaag tatcaagcct ctgaaaacac cttggggctt      60
aatcctgtcg ttgggctgcg tggaaaggat ctactggctt ctgctcgaat ggtgcttagg     120
caggccatca agcaaccggt gcacagcgtc aaacatgtcg cgcactttgg tcttgaactc     180
aagaacgtac tgctgggtaa atccgggctg caaccgacca gcgatgaccg tcgcttcgcc     240
gatccggcct ggagccagaa cccgctctat aaacgttatt gcaaaccta cctggcgtgg     300 cgcaaggaac tccacgactg gatcgatgaa agtaacctcg cccccaagga tgtgcgcgt      360 gggcacttcg tgatcaacct catgaccgaa gccatggcgc cgaccaacac cgcggccaac     420
```

```
ccggcggcag tcaaacgctt tttcgaaacc ggtggcaaaa gcctgctcga cggcctctcg    480
cacctggcca aggatctggt acacaacggc ggcatgccga gccaggtcaa catgggtgca    540
ttcgaggtcg gcaagagcct gggcgtgacc gaaggcgcgg tggtgtttcg caacgatgtg    600
ctggaactga tccagtacaa gccgaccacc gagcaggtat acgaacgccc gctgctggtg    660
gtgccgccgc agatcaacaa gttctacgtt tcgacctga gcccggacaa gagcctggcg    720
cggttctgcc tgcgcaacaa cgtgcaaacg ttcatcgtca gctggcgaaa tcccaccaag    780
gaacagcgag agtggggcct gtcgacctac atcgaagccc tcaaggaagc ggttgatgtc    840
gttaccgcga tcaccggcag caaagacgtg aacatgctcg gcgcctgctc cggcggcatc    900
acttgcaccg cgctgctggg ccattacgcg gcgattggcg aaaacaaggt caacgccctg    960
accttgctgg tgagcgtgct tgataccacc ctcgacagcg atgttgccct gttcgtcaat    1020
gaacagaccc ttgaagccgc caagcgccac tcgtaccagg ccggcgtact ggaaggccgc    1080
gacatggcga aggtcttcgc ctggatgcgc cccaacgatc tgatctggaa ctactgggtc    1140
aacaattacc tgctaggcaa cgaaccgccg tgttcgaca tcctgttctg gaacaacgac    1200
accacacggt tgcccgcggc gttccacggc gacctgatcg aactgttcaa aaataaccca    1260
ctgattcgcc cgaatgcact ggaagtgtgc ggcacccca tcgacctcaa gcaggtgacg    1320
gccgacatct tttccctggc cggcaccaac gaccacatca cccgtggaa gtcctgctac    1380 aagtcggcgc aactgtttgg cggcaacgtt gaattcgtgc tgtcgagcag cgggcatatc    1440
cagagcatcc tgaacccgcc gggcaatccg aaatcgcgct acatgaccag caccgaagtg    1500
gcggaaaatg ccgatgaatg caagcgaat gccaccaagc ataccgattc ctggtggctg    1560
cactggcagc cctggcaggc ccaacgctcg gcgagctga aaagtcccc gacaaaactg    1620 ggcagcaagg cgtatccggc aggtgaagcg gcgccaggca cgtacgtgca cgaacggtaa    1680
```

<210> SEQ ID NO 3
<211> LENGTH: 560
<212> TYPE: PRT
<213> ORGANISM: Pseudomonas cichorii YN2; FERM BP-7375

<400> SEQUENCE: 3

```
Met Arg Asp Lys Pro Ala Arg Glu Ser Leu Pro Thr Pro Ala Lys Phe
 1               5                  10                  15

Ile Asn Ala Gln Ser Ala Ile Thr Gly Leu Arg Gly Arg Asp Leu Val
            20                  25                  30

Ser Thr Leu Arg Ser Val Ala Ala His Gly Leu Arg His Pro Val His
        35                  40                  45

Thr Ala Arg His Ala Leu Lys Leu Gly Gly Gln Leu Gly Arg Val Leu
    50                  55                  60

Leu Gly Asp Thr Leu His Pro Thr Asn Pro Gln Asp Arg Arg Phe Asp
65                  70                  75                  80

Asp Pro Ala Trp Ser Leu Asn Pro Phe Tyr Arg Arg Ser Leu Gln Ala
                85                  90                  95

Tyr Leu Ser Trp Gln Lys Gln Val Lys Ser Trp Ile Asp Glu Ser Asn
            100                 105                 110

Met Ser Pro Asp Asp Arg Ala Arg Ala His Phe Ala Phe Ala Leu Leu
        115                 120                 125

Asn Asp Ala Val Ser Pro Ser Asn Ser Leu Leu Asn Pro Leu Ala Ile
    130                 135                 140

Lys Glu Ile Phe Asn Ser Gly Gly Asn Ser Leu Val Arg Gly Ile Gly
```

```
                145                 150                 155                 160
His Leu Val Asp Asp Leu Leu His Asn Asp Gly Leu Pro Arg Gln Val
                165                 170                 175
Thr Arg His Ala Phe Glu Val Gly Lys Thr Val Ala Thr Thr Thr Gly
                180                 185                 190
Ala Val Val Phe Arg Asn Glu Leu Leu Glu Leu Ile Gln Tyr Lys Pro
                195                 200                 205
Met Ser Glu Lys Gln Tyr Ser Lys Pro Leu Leu Val Val Pro Pro Gln
                210                 215                 220
Ile Asn Lys Tyr Tyr Ile Phe Asp Leu Ser Pro His Asn Ser Phe Val
225                 230                 235                 240
Gln Phe Ala Leu Lys Asn Gly Leu Gln Thr Phe Val Ile Ser Trp Arg
                245                 250                 255
Asn Pro Asp Val Arg His Arg Glu Trp Gly Leu Ser Thr Tyr Val Glu
                260                 265                 270
Ala Val Glu Glu Ala Met Asn Val Cys Arg Ala Ile Thr Gly Ala Arg
                275                 280                 285
Glu Val Asn Leu Met Gly Ala Cys Ala Gly Gly Leu Thr Ile Ala Ala
                290                 295                 300
Leu Gln Gly His Leu Gln Ala Lys Arg Gln Leu Arg Arg Val Ser Ser
305                 310                 315                 320
Ala Thr Tyr Leu Val Ser Leu Leu Asp Ser Gln Leu Asp Ser Pro Ala
                325                 330                 335
Thr Leu Phe Ala Asp Glu Gln Thr Leu Glu Ala Ala Lys Arg Arg Ser
                340                 345                 350
Tyr Gln Lys Gly Val Leu Glu Gly Arg Asp Met Ala Lys Val Phe Ala
                355                 360                 365
Trp Met Arg Pro Asn Asp Leu Ile Trp Ser Tyr Phe Val Asn Asn Tyr
                370                 375                 380
Leu Met Gly Lys Glu Pro Pro Ala Phe Asp Ile Leu Tyr Trp Asn Asn
385                 390                 395                 400
Asp Asn Thr Arg Leu Pro Ala Ala Leu His Gly Asp Leu Leu Asp Phe
                405                 410                 415
Phe Lys His Asn Pro Leu Ser His Pro Gly Gly Leu Glu Val Cys Gly
                420                 425                 430
Thr Pro Ile Asp Leu Gln Lys Val Thr Val Asp Ser Phe Ser Val Ala
                435                 440                 445
Gly Ile Asn Asp His Ile Thr Pro Trp Asp Ala Val Tyr Arg Ser Thr
                450                 455                 460
Leu Leu Leu Gly Gly Glu Arg Arg Phe Val Leu Ala Asn Ser Gly His
465                 470                 475                 480
Val Gln Ser Ile Leu Asn Pro Pro Asn Asn Pro Lys Ala Asn Tyr Leu
                485                 490                 495
Glu Gly Ala Lys Leu Ser Ser Asp Pro Arg Ala Trp Tyr Tyr Asp Ala
                500                 505                 510
Lys Pro Val Asp Gly Ser Trp Trp Thr Gln Trp Leu Gly Trp Ile Gln
                515                 520                 525
Glu Arg Ser Gly Ala Gln Lys Glu Thr His Met Ala Leu Gly Asn Gln
                530                 535                 540
Asn Tyr Pro Pro Met Glu Ala Ala Pro Gly Thr Tyr Val Arg Val Arg
545                 550                 555                 560

<210> SEQ ID NO 4
```

<211> LENGTH: 1683
<212> TYPE: DNA
<213> ORGANISM: Pseudomonas cichorii YN2; FERM BP-7375

<400> SEQUENCE: 4

| | | | | | |
|---|---|---|---|---|---|
| atgcgcgata | aacctgcgag | ggagtcacta | cccaccccg | ccaagttcat | caacgcacaa | 60 |
| agtgcgatta | ccggcctgcg | tggccgggat | ctggtttcga | ctttgcgcag | tgtcgccgcc | 120 |
| catggcctgc | gccaccccgt | gcacaccgcg | cgacacgcct | tgaaactggg | tggtcaactg | 180 |
| ggacgcgtgt | tgctgggcga | caccctgcat | cccaccaacc | cgcaagaccg | tcgcttcgac | 240 |
| gatccggcgt | ggagtctcaa | tcccttttat | cgtcgcagcc | tgcaggcgta | cctgagctgg | 300 |
| cagaagcagg | tcaagagctg | gatcgacgaa | agcaacatga | gcccggatga | ccgcgcccgt | 360 |
| gcgcacttcg | cgttcgccct | gctcaacgat | gccgtgtcgc | cgtccaacag | cctgctcaat | 420 |
| ccgctggcga | tcaaggaaat | cttcaactcc | ggcggcaaca | gcctggtgcg | cgggatcggc | 480 |
| catctggtcg | atgacctctt | gcacaacgat | ggcttgcccc | ggcaagtcac | caggcatgca | 540 |
| ttcgaggttg | gcaagaccgt | cgccaccacc | accggcgccg | tggtgtttcg | caacgagctg | 600 |
| ctggagctga | tccaatacaa | gccgatgagc | gaaaagcagt | attccaaacc | gctgctggtg | 660 |
| gtgccgccac | agatcaacaa | gtactacatt | tttgacctca | gccccataa | cagcttcgtc | 720 |
| cagttcgcgc | tcaagaacgg | cctgcaaacc | ttcgtcatca | gctggcgcaa | tccggatgta | 780 |
| cgtcaccgcg | aatgggggcct | gtcgacctac | gtcgaagcgg | tggaagaagc | catgaatgtc | 840 |
| tgccgggcaa | tcaccggcgc | gcgcgaggtc | aacctgatgg | gcgcctgcgc | tggcgggctg | 900 |
| accattgctg | ccctgcaggg | ccacttgcaa | gccaagcgac | agctgcgccg | cgtctccagc | 960 |
| gcgacgtacc | tggtgagcct | gctcgacagc | caactggaca | gcccggccac | actcttcgcc | 1020 |
| gacgaacaga | ccctggaggc | ggccaagcgc | cgctcctacc | agaaaggtgt | gctggaaggc | 1080 |
| cgcgacatgg | ccaaggtttt | cgcctggatg | cgccccaacg | atttgatctg | gagctacttc | 1140 |
| gtcaacaatt | acctgatggg | caaggagccg | ccggcgttcg | acattctcta | ctggaacaat | 1200 |
| gacaacacac | gcctgccggc | cgccctgcat | ggtgacttgc | tggacttctt | caagcacaac | 1260 |
| ccgctgagcc | atccgggtgg | cctggaagtg | tgcggcaccc | cgatcgactt | gcaaaaggtc | 1320 |
| accgtcgaca | gtttcagcgt | ggccggcatc | aacgatcaca | tcacgccgtg | ggacgcggtg | 1380 |
| tatcgctcaa | ccctgttgct | cggtggcgag | cgtcgctttg | tcctggccaa | cagcggtcat | 1440 |
| gtgcagagca | ttctcaaccc | gccgaacaat | ccgaaagcca | actacctcga | aggtgcaaaa | 1500 |
| ctaagcagcg | accccagggc | ctggtactac | gacgccaagc | ccgtcgacgg | tagctggtgg | 1560 |
| acgcaatggc | tgggctggat | tcaggagcgc | tcgggcgcgc | aaaaagaaac | ccacatggcc | 1620 |
| ctcggcaatc | agaattatcc | accgatggag | gcggcgcccg | ggacttacgt | gcgcgtgcgc | 1680 |
| tga | | | | | | 1683 |

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:Primer for PCR multiplication

<400> SEQUENCE: 5
tgctggaact gatccagtac                    20

<210> SEQ ID NO 6

```
<211> LENGTH: 23
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 6
gggttgagga tgctctggat gtg                                          23

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 7
ggaccaagct tctcgtctca gggcaatgg                                    29

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 8
cgagcaagct tgctcctaca ggtgaaggc                                    29

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 9
gtattaagct tgaagacgaa ggagtgttg                                    29

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 10
catccaagct tcttatgatc gggtcatgcc                                   30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 11
cgggatccag taacaagagt aacgatgagt                                   30

<210> SEQ ID NO 12
<211> LENGTH: 30
```

```
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 12
cgatctcgag ttaccgttcg tgcacgtacg                                       30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 13
cgggatcccg cgataaacct gcgagggagt                                       30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:Primer for
      PCR multiplication

<400> SEQUENCE: 14
cgatctcgag gcgcacgcgc acgtaagtcc                                       30
```